(12) United States Patent
Silvestre et al.

(10) Patent No.: US 11,779,619 B2
(45) Date of Patent: Oct. 10, 2023

(54) ONCOLYTIC VIRUS FOR EXPRESSION OF IMMUNE CHECKPOINT MODULATORS

(71) Applicant: Transgene SA, Illkirch Graffenstaden (FR)

(72) Inventors: Nathalie Silvestre, Ergersheim (FR); Michel Geist, Brumath (FR); Karola Rittner, Strasbourg (FR); Jean-Baptiste Marchand, Obernai (FR); Christine Thioudellet, Strasbourg (FR)

(73) Assignee: Transgene SA, Illkirch Graffenstaden (FR)

( * ) Notice: Subject to any disclaimer, the term of this patent is extended or adjusted under 35 U.S.C. 154(b) by 777 days.

(21) Appl. No.: 16/725,485

(22) Filed: Dec. 23, 2019

(65) Prior Publication Data

US 2020/0197457 A1 Jun. 25, 2020

Related U.S. Application Data

(63) Continuation of application No. 15/325,562, filed as application No. PCT/EP2015/066263 on Jul. 16, 2015, now Pat. No. 10,555,981.

(30) Foreign Application Priority Data

Jul. 16, 2014 (EP) .................................... 14306153

(51) Int. Cl.
| | |
|---|---|
| *A61K 35/768* | (2015.01) |
| *C07K 16/28* | (2006.01) |
| *C12N 15/863* | (2006.01) |
| *A61K 9/00* | (2006.01) |
| *C07K 14/535* | (2006.01) |
| *A61K 39/00* | (2006.01) |
| *A61K 35/763* | (2015.01) |
| *A61K 35/761* | (2015.01) |
| *A61K 47/02* | (2006.01) |
| *A61K 9/08* | (2006.01) |
| *C12N 7/00* | (2006.01) |
| *C12N 9/10* | (2006.01) |
| *C12N 9/80* | (2006.01) |

(52) U.S. Cl.
CPC .......... *A61K 35/768* (2013.01); *A61K 9/0019* (2013.01); *C07K 14/535* (2013.01); *C07K 16/2818* (2013.01); *C07K 16/2896* (2013.01); *C12N 15/8636* (2013.01); *C12Y 204/02009* (2013.01); *A61K 9/08* (2013.01); *A61K 35/761* (2013.01); *A61K 35/763* (2013.01); *A61K 47/02* (2013.01); *A61K 2039/505* (2013.01); *A61K 2039/5256* (2013.01); *C07K 2317/51* (2013.01); *C07K 2317/515* (2013.01); *C07K 2317/55* (2013.01); *C07K 2317/622* (2013.01); *C07K 2317/76* (2013.01); *C12N 7/00* (2013.01); *C12N 9/1077* (2013.01); *C12N 9/80* (2013.01); *C12N 2710/24121* (2013.01); *C12N 2710/24132* (2013.01); *C12N 2799/023* (2013.01); *C12Y 305/01023* (2013.01)

(58) Field of Classification Search
CPC .. A61K 35/768; A61K 9/0019; C07K 14/535; C07K 16/2818; C07K 16/2896; C12N 15/8636; C12N 2799/023; C12Y 204/02009
USPC ............... 424/199.1, 209.1, 93.6; 435/320.1; 530/388.22
See application file for complete search history.

(56) References Cited

U.S. PATENT DOCUMENTS

| | | |
|---|---|---|
| 5,225,539 A | 7/1993 | Winter |
| 5,457,035 A | 10/1995 | Baum et al. |
| 5,530,101 A | 6/1996 | Queen et al. |
| 5,773,578 A | 6/1998 | Hercend et al. |
| 6,180,370 B1 | 1/2001 | Queen et al. |
| 6,984,720 B1 | 1/2006 | Korman et al. |
| 7,109,003 B2 | 9/2006 | Hanson et al. |
| 7,291,331 B1 | 11/2007 | Croft et al. |
| 7,622,444 B2 | 11/2009 | Weinberg |
| 7,858,746 B2 | 12/2010 | Honjo et al. |
| 8,017,114 B2 | 9/2011 | Korman et al. |
| 8,143,379 B2 | 3/2012 | Hanson et al. |
| 8,491,895 B2 | 7/2013 | Hanson et al. |
| 9,687,515 B2 * | 6/2017 | Erbs ..................... A61K 31/555 |
| 10,555,981 B2 * | 2/2020 | Silvestre .............. C07K 14/535 |
| 2013/0177557 A1 | 7/2013 | Noelle et al. |

(Continued)

FOREIGN PATENT DOCUMENTS

| | | |
|---|---|---|
| EA | 013615 | 12/2007 |
| EP | 1 907 000 B1 | 4/2008 |
| WO | WO 97/20574 | 6/1997 |

(Continued)

OTHER PUBLICATIONS

Guse et al. (2011) Exp. Opin. Biol. Ther.:doi:10.1517/14712598 .2011.558838, pp. 1-14.*

(Continued)

*Primary Examiner* — Anne Marie S Wehbe
(74) *Attorney, Agent, or Firm* — Panitch Schwarze Belisario & Nadel LLP; Eric M. Dunston

(57) ABSTRACT

The present invention provides an oncolytic virus comprising nucleotide sequence(s) encoding one or more immune checkpoint modulator(s). It also concerns a pharmaceutical composition comprising effective amount of said oncolytic virus and, eventually, a pharmaceutically acceptable vehicle and its use for treating proliferative diseases such as cancers.

21 Claims, 7 Drawing Sheets

Specification includes a Sequence Listing.

(56) References Cited

U.S. PATENT DOCUMENTS

2015/0250837 A1* 9/2015 Nolin .................. A61K 35/761
　　　　　　　　　　　　　　　　　　　　　　435/235.1

FOREIGN PATENT DOCUMENTS

| WO | WO 03/045197 | 6/2003 |
| --- | --- | --- |
| WO | WO 03/082919 | 10/2003 |
| WO | WO 03/106498 | 12/2003 |
| WO | WO 2004/004771 | 1/2004 |
| WO | WO 2004/056875 | 7/2004 |
| WO | WO 2006/121168 | 11/2006 |
| WO | WO 2007/123737 | 11/2007 |
| WO | WO 2008/156712 | 12/2008 |
| WO | WO 2009/014708 | 1/2009 |
| WO | WO 2009/065546 | 5/2009 |
| WO | WO 2009/065547 | 5/2009 |
| WO | WO 2009/114335 | 9/2009 |
| WO | WO 2012/110360 | 8/2012 |
| WO | WO 2013/043569 | 3/2013 |
| WO | WO 2014/022138 | 2/2014 |
| WO | WO 2014/047350 | * 3/2014 |
| WO | WO 2020/0049001 | 3/2020 |

OTHER PUBLICATIONS

Burke et al. (2010) Cytokine & Growth Factor Reviews, vol. 21, 149-151.*
Bauzon et al. (Feb. 1, 2014), Frontiers in Immunology, vol. 5, 1-10.*
Gammon et al. (2010) PloS Pathogens, vol. 6(7), 1-20.*
Foloppe et al. (2008) Gene Therapy, vol. 15, 1361-1371.*
Kan et al., *Generation of an attenuated Tiantan vaccina virus by deletion of ribonucleotide reductase large submit*, 159 Arch. Virol 2223-2231 (2014).
Agata et al., *Expression of the PD-1 antigen on the surface of stimulated mouse T and B lymphocytes*, 8(5) International Immunology 765-772 (1996).
Andtbacka et al., *OPTiM; A randomized phase III trial of talimogene laherparepvec (T-VEC) versus subcutaneous (SC) granulocyte-macrophage colony-stimulating factor (GM-CSF) for the treatment of (tx) of unresected stage IIIB/C and IV melanoma*, 31 J. Clin Oncol 1-2 (2013).
Bauzon et al., *Armed therapeutic viruses—a disruptive therapy on the horizon of cancer immunotherapy*, 5(74) Frontiers in Immunology 1-10 (Feb. 24, 2014).
Bedke et al., *Targeted therapy in renal cell carcinoma: moving from molecular agents to specific immunotherapy*, 32 World J. Urol 31-38 (2014).
Bennett et al., *Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses*, 170 J. Immunol 711-718 (2003).
Blank et al., *Interaction of PD-L1 on tumor cells with PD-1 on tumor-specific T cells as a mechanism of immune evasion: implications for tumor immunotherapy*, 54 Cancer Immunol Immunother 307-314 (2005).
Blank, C.U., *The perspective of immunotherapy: new molecules and new mechanisms of action in immune modulation*,26(2) Co-Oncology 204-214 (Mar. 2014).
Boviatsis et al., *Antitumor activity and reporter gene transfer into rat brain neoplasms inoculated with herpes simplex virus vectors defective in thymidine kinase or ribonucleotide reductase*, 1(5) Gene Therapy 323-331 (Sep. 1994).
Breitbach et al., *Targeted and Armed Oncolytic Poxviruses for Cancer: the Lead Example of JX-594*, 13 Current Pharmaceutical Biotechnology 1768-1772 (2012).
Broyles, S., *Vaccinia Virus Encodes a functional of dUTPase*, 195 Virology 863-865 (1993).
Brunet et al., *A new member of the immunoglobulin superfamily—CTLA-4*, 328 Nature 267-270 (Jul. 16, 1987).
Cohen et al., ONYX-015 Onyx Pharmaceuticals, 2(12) Current Opinion in Investigational Drugs 1770-1775 (2001).
Carter et al., *PD-1:PD-L inhibitory pathway affects both $CD4^+$ and $CD8^+T$ cells and is overcome by IL-2*, 32 Eur. J. Immunol 634-643 (2002).
Chambers et al., *Comparison of genetically engineered herpes simplex viruses for the treatment of brain tumors in a scid mouse model of human malignant glioma*, 92 Proc. Natl. Acad. Sci 1411-1415 (Feb. 1995).
Champiat et al., *Incorporating Immune-Checkpoint Inhibitors into Systemic Therapy of NSCLC*, 9(2) Journal of Thoracic Oncology 144-153 (Feb. 2014).
G. Cory et al., *Regulation of ribonucleotide reductase activity in mammalian cells*, 53-54(1-2) Mol. Cell. Biochem. 257-266 (1983) (Abstract).
Darivach et al., *Human Ig superfamily CTLA-4 gene: chromosomal localization and identity of protein sequence between murine and human CTLA-4 cytoplasmic domains*, 18 Eur. J. Immunol. 1901-1905 (1988).
Chernajovsky et al., *Fighting cancer with oncolytic viruses*, 332 BMJ 170-172 (Jan. 21, 2006).
Dias et al., *Targeted cancer immunotherapy with oncolytic adenovirus coding for a fully human monoclonal antibody specific for CTLA-4*, Gene Therapy 1-11 (2011).
Dias et al., *Targeted Chemotherapy for Head and Neck Cancer with a Chimeric Oncolytic Adenovirus Coding for Bifunctional Suicide Protein FCU1*, 16(9) Clin Cancer Res 2540-2549 (May 1, 2010).
Dong et al., *B7-H1 pathway and its role in the evasion of tumor immunity*, 81 J. Mol Med 281-287 (2003).
Dong et al., *Tumor-associated B7-H1 promotes T-cell apoptosis: A potential mechanism of immune evasion*, 8(8) Nature Medicine 793-800 (Aug. 2002).
Du et al., *Tumor-specific oncolytic adenoviruses expressing granulocyte macrophage colony-stimulating factor or anti-CTLA4 antibody for the treatment of cancers*, 21 Cancer Gene Therapy 340-348 (2014).
Duxbury et al., *RNA interference targeting the M2 subunit of ribonucleotide reductase enhances pancreatic adenocarcinoma chemosensitivity to gemcitabine*, 23 Oncogene 1539-1549 (2004).
H. L. Elford et al., *Effect of Methotrexate and 5-Fluorodeoxyuridine on Robinucleotide Reductase Activity in Mammalian Cells*, 37 Cancer Research 4389-4394 (Dec. 1977).
Engeland et al., *CTLA-4 and PD-L1 Checkpoint Blockade Enhances Oncolytic Measles Virus Therapy*, 22(11) Molecular Therapy 1949-1959 (Nov. 2014).
Engeland et al., *Measles Virus Mediated Immune Checkpoint Blockade Enhances Cancer Immunovirotherapy*, 22(Supplement 1) Molecular Therapy (May 2014) (abstract only).
Foloppe et al., *Targeted delivery of a suicide gene to human colorectal tumors by a conditionally replicating vaccine virus*, 15 Gene Therapy 1361-1371 (2008).
Freeman et al., *Engagement of the PD-1 Immunoinhibitory Receptor by a Novel B7 Family Member Leads to Negative Regulation of Lymphocyte Activation*, 192(7) J. Exp. Med. 1027-1034 (Oct. 2, 2000).
Freeman et al., *Phase I/II Trial of Intravenous NDV-HUJ Oncolytic Virus in Recurrent Glioblastoma Multiforme*, 13(1) Molecular Therapy 21-228 (Jan. 2006).
Gammon et al., *Vaccinia Virus-Encoded Ribonucleotide Reductase Subunits Are Differentially Required for Replication and Pathogenesis*, 6(7) PLoS Pathogens 1-20 (Jul. 2010).
Geevarghese et al., *Phase I/II Study of Oncolytic Herpes Simplex Virus NV1020 in Patients with Extensively Pretreated Refractory Colorectal Cancer Metastatic to the Liver*, 21 Human Gene Therapy 1119-1128 (Sep. 2010).
Guse et al., *Oncolytic vaccinia virus for the treatment of cancer*, 11(3) Expert Opin. Biol. Ther. 595-608 (2011).
Guse et al., *Oncolytic vaccinia virus for the treatment of cancer*, Expert Opinion on Biological Therapy 1-14 (Feb. 2011).
Hermiston, T., *A demand for next-generation oncolytic adenovirus*, 8(4) Current Opinion in Molecular Therapeutics 322-330 (Aug. 2006).

(56) References Cited

OTHER PUBLICATIONS

Jun et al., *Generation of antagonistic anti-TIM-3 and anti-LAG-3 monoclonal antibodies for potential nvoal immunotherapy combitnations*, AnaptysBio (2014).
Kaufmann et al., *Chemovirotherapy of Malignant Melanoma with a Targeted and Armed Oncoytic Measles Virus*, 133 Journal of Investigative Dermatology 1034-1042 (2013).
Khuri et al., *A controlled trial of intratumoral ONYX-015, a selectively-replicating adenovirus, in combination with cisplatin and 5-fluorouracil in patients with recurrent head and neck cancer*, 6(8) Nature Medicine 879-885 (Aug. 2000).
Kirn et al., *Replication-selective virotherapy for cancer: Biological principles, risk management and future directions*, 7(7) Nature Medicine 781-787 (Jul. 2001).
Kirn et al., *Targeted and armed oncolytic poxviruses: a novel multi-mechanistic therapeutic class for cancer*, 9 Nature 64-71 (Jan. 2009).
P. Kleinpeter et al., *Vectorization in an oncolytic vaccinia virus of an antibody, a Fab and a scFv against programmed cell death-1 (PD-1) allows their intratumoral delivery and an improved tumor-growth inhibition*, 5(10) Oncoimmunology 1-14 e1220467-e1220467-14 (2016).
P. Kleinpeter et al., *By Binding CD80 and CD86, the Vaccinia Virus M2 Protein Blocks Their Interactions with both CD28 and CTLA4 and Potentiates CD80 Binding to PD-L1*, 93(11) Journal of Virology 1-18 (Jun. 2019).
Leach et al., *Enhancement of Antitumor Immunity by CTLA-4 Blockade*, 271 Science 1734-1736 (Mar. 22, 1996).
Lorence et al., *Phase 1 Clinical Experience Using Intravenous Administration of PV701, an Oncolytic Newcastle Disease Virus*, 7 Current Cancer Drug Targets 157-167 (2007).
Madan et al., *Ipilimumab and a poxiviral vaccine targeting prostate-specific antigen in metastatic castration-resistant protate cancer: a phase 1 dose escalation trial*, Articles 1-8 (Feb. 10, 2012).
Madan et al., *Combination of vaccine and immune checkpoint inhibitor is safe with encouraging clinical activity*, 1(7) OncoImmunology 1167-1168 (Oct. 2012).
Martuza et al., *Experimental Therapy of Human Glioma by Means of a Genetically Engineered Virus Mutant*, 252 Science 854-856 (Oct. 3, 1990).
McDonald et al., *A measles virus vaccine strain derivative as a novel oncolytic agent against breast cancer*, 99 Breast Cancer Research and Treatment 177-184 (2006).
Mineta et al, *Treatment of Malignant Gliomas Using Ganciclovir-hypersensitive, Ribonucleotide Reductase-deficient Herpes Simplex Viral Mutant*, 54 Cancer Research 3963-3966 (Aug. 1, 1994).
Okazaki et al., *New regulatory co-receptors: Inducible co-stimulator and PD-1*, 17 Autoimmunity 779-782 (2002).
Phuangsab et al., *Newcastle disease virus therapy of human tumor xenografts: antitumor effects of local or systemic administration*, 172 Cancer Letters 27-36 (2001).
Potts et al., *Oncolytic viruses in the Treatment of Bladder Cancer*, 2012 Advanced in Urology 1-11 (2012).
Presta et al., *Humanization of an Anti-Vascular Endothelial Growth Factor Monoclonal Antibody for the Therapy of Solid Tumors and Other Disorders*, 57 Cancer Research 4593-4599 (Oct. 15, 1997).
Pyles et al., *Evidence that the Herpes Simplex Virus Type 1 Uracil DNA Glycosylase Is Required for Efficient Viral Replication and Latency in the Murine Nervous System*, 68(8) Journal of Virology 4963-4972 (Aug. 1994).
Qureshi et al., *Trans-endocytosis of CD80 and CD86: a molecular basis for the cell extrinsic function of CTLA-4*, 332(6029) Science 600-603 (2011).

Rudlin et al., *Phase 1 Clinical Study of Seneca Valley Virus (SVV-001), a Replication-Competent Picornavirus, in Advance Solid Tumors with Neuroendocrine Features*, 17(4) Clin Cancer Res 888-895 (Feb. 15, 2011).
Russian Inquiry with English Translation dated Aug. 22, 2018.
Senzer et al., *Phase II Clinical Trial of a Granulocyte-Macrophase Colony-Stimulating Factor-Encoding, Second-Generation Oncolytic Herpesvirus in Patents with Unresectable Metastatic Melanoma*, 27(34) Journal of Clinical Oncology 5763-5771 (Dec. 1, 2009).
Shi et al., *Tumor-specific oncolytic adenoviruses expressing granulocyte macrophage colony-stimulating factor or anti-CTLA4 anitbody for the treatment of cancers*, 21 Cancer Gene Therapy 340-348 (2014).
Stojdl et al., *Exploiting tumor-specific defects in the interferon pathway with a previously unknown oncolytic virus*, 6(7) Nature Medicine 821-825 (Jul. 2000).
Stojdl et al., *VSV strains with defects in their ability to shutdown innate immunity are potent systemic anti-cancer agents*, 4 Cancer Cell 263-275 (2003).
Thorne, S.H. et al., *Immunotherapeutic potential of oncolytic vaccinia virus*, 4 Frontiers In Oncology 1-5 (Jun. 2014).
Thorne et al., *Rational strain selection and engineering creates a broad-spectrum, systemically effective oncolytic poxvirus, JX-963*, 117(11) The Journal of Clinical Investigation 3350-3358 (Nov. 2007).
Topalian et al., *Targeting the PD-1/B7-H1(PD-L1) pathway to activate anti-tumor immunity*, 24(2) Curr. Opin. Immunol. 207-212 (Apr. 2012).
Wang et al., *VISTA, a novel mouse Ig superfamily ligand that negatively regulates T cell responses*, 208(3) J. Exp. Med. 577-592 (Mar. 14, 2011).
Wong et al., *Oncolytic Viruses for Cancer Therapy: Overcoming the Obstacles*, 2 Viruses 78-106 (2010).
Xia, et al., *Phase III randomized clinical trial on intratumoral injection of E1B gene-deleted adenovirus(H101) combined with cispliatin-based chemotherapy in treating squamous cell cancer of head and neck or esophagus*, 23(12) Al Zheng 1666-1670 (Dec. 2004) (abstract only).
Zhang et al., *Eradication of Solid Human Breast Tumors in Nude Mice with an Intravenously Inject Light-Emitting Oncolytic Vaccinia Virus*, 67(20) Cancer Research 10038-10046 (Oct. 15, 2007).
International Search Report dated Sep. 9, 2015, and Written Opinion in corresponding PCT Application No. PCT/EP2015/066353.
*Anti-tumoral effect of a vaccinia virus VV-TK⁻-RR⁻J43, encoding murine monoclonal anti-PD1 antibody J43*, Annex 1 (May 11, 2018).
*Comparative analysis of the replication capacity of three vaccinia viruses in primary versus cancerous cells: the Vaccinia virus VVTG17137 deleted for I4L gene compared to VVTG15466 and VVTG17101 with intact I4L gene, in human hepatocellular carcinoma cells and human primary hepatocytes*, Annex 2 (May 11, 2018).
Burrell et al., *Principles of Virology*, Chapter 4 of Fenner and White's Medical Virology 39-55 (2017).
Chinchar, *Replication of Viruses*, Department of Microbiology 1471-1478 (1999).
Liu et al., *Deletion of C7L and K1L Genes Leads to Significantly Decreased Virulence of Recombinant Vaccinia Virus Tian Tan*, 8(7) PLOS One 1-13 (Jul. 2013).
Shisler et al., *Vaccinia Virus Serpin-1 Deletion Mutant Exhibits a Host Range Defect Characterized by Low Levels of Intermediate and Late mRNAs*, 262 Virology 298-311 (1999).

\* cited by examiner

R : reduced condition
NR : Non reduced condition

Figure 4

Heavy chain J43 sequence:

MGLGLQWVFFVALLKGVHCEVRLLESGGGLVKPEGSLKLSCVASGFTFSD

YFMSWVRQAPGKGLEWVAHIYTKSYNYATYYSGSVKGRFTISRDDSRSMV

YLQMNNLRTEDTATYYCTRDGSGYPSLDFWGQGTQVTVSSATTTAPSVYP

LAPACDSTTSTTDTVTLGCLVKGYFPEPVTVSWNSGALTSGVHTFPSVLH

SGLYSLSSSVTVPSSTWPKQPITCNVAHPASSTKVDKKIEPRTDTDTCPN

PPDPCPTCPTPDLLGGPSVFIFPPKPKDVLMISLTPKITCVVVDVSEEEP

DVQFNWYVNNVEDKTAQTETRQRQYNSTYRVVSVLPIKHQDWMSGKVFKC

KVNNNALPSPIEKTISKPRGQVRVPQIYTFPPPIEQTVKKDVSVTCLVTG

FLPQDIHVEWESNGQPQPEQNYKNTQPVLDSDGSYFLYSKLNVPKSRWDQ

GDSFTCSVIHEALHNHHMTKTISRSLGN

Light chain J43 sequence:

MAWTPGIFMVLSYLTGSFSYELTQPPSASVNVGETVKITCSGDQLPKYFA

DWFHQRSDQTILQVIYDDNKRPSGIPERISGSSSGTTATLTIRDVRAEDE

GDYYCFSGYVDSDSKLYVFGSGTQLTVLGGPKSSPKVTVFPPSPEELRTN

KATLVCLVNDFYPGSATVTWKANGATINDGVKTTKPSKQGQNYMTSSYLS

LTADQWKSHNRVSCQVTHEGETVEKSLSPAECL

ONCOLYTIC VIRUS FOR EXPRESSION OF IMMUNE CHECKPOINT MODULATORS

CROSS-REFERENCE TO RELATED APPLICATIONS

This application is a Continuation Application of U.S. patent application Ser. No. 15/325,562, filed on Jan. 11, 2017, which is a U.S. National Stage Application pursuant to 35 U.S.C. § 371 of International Patent Application PCT/EP2015/066263, filed on Jul. 16, 2015, and published as WO 2016/008976 on Jan. 21, 2016, which claims priority to European Patent Application 14306153.9, filed on Jul. 16, 2014, all of which are incorporated herein by reference in their entireties for all purposes.

FIELD OF THE INVENTION

The present invention generally relates to the field of oncolytic virotherapy and more specifically to compositions and methods to treat, prevent, or inhibit proliferative diseases, especially cancer. Embodiments include an oncolytic virus comprising nucleotide sequence(s) encoding one or more immune checkpoint modulator(s). Embodiments also include a pharmaceutical composition comprising such oncolytic virus and, eventually, a pharmaceutically acceptable vehicle and its use for treating proliferative diseases such as cancers.

Cancer is caused by both external factors (e.g. tobacco, infectious organisms, alimentary habits, chemicals, and radiation) and internal factors (e.g. inherited mutations, hormones, immune conditions, and mutations that occur from metabolism). Each year, cancer is diagnosed in more than 12 million subjects worldwide. In industrialized countries, approximately one person out five will die of cancer. Although a vast number of chemotherapeutics exist, they are often ineffective, especially against malignant and metastatic tumors that establish at a very early stage of the disease. Moreover, antitumor immunity is often ineffective due to the fact that tumor cells have evolved mechanisms to escape host defense. One of the major mechanisms of immune suppression is a process known as "T-cell exhaustion", which results from chronic exposure to antigens and is characterized by the upregulation of inhibitory receptors. These inhibitory receptors serve as immune checkpoints in order to prevent uncontrolled immune reactions. Various immune checkpoints acting at different levels of T cell immunity have been described in the literature, including programmed cell death protein 1 (PD-1) and its ligands PD-L1 and PD-L2, CTLA-4 (cytotoxic T-lymphocyte associated protein-4), LAG3, B and T lymphocyte attenuator, T-cell immunoglobulin, mucin domain-containing protein 3 (TIM-3), and V-domain immunoglobulin suppressor of T cell activation.

Whatever the mechanism of action, these immune checkpoints can inhibit the development of an efficient anti-tumor immune response. There is increasing interest in the possible therapeutic benefits of blocking such immune checkpoints as a means of inhibiting immune system tolerance to tumors and thus rescue exhausted antitumor T cells (Leach et al., 1996, Science 271: 1734-6). A vast number of antagonistic antibodies have been developed during the last decade (e.g. anti Tim3, -PD-L1, -CTLA-4, -PD1, etc.) and most importantly, some have been associated with objective clinical responses in cancer patients. Antibodies targeting CTLA-4 are already marketed (e.g. Ipilimumab, Yervoy, Bristol-Myers Squibb) for metastatic melanoma. BMS reported that from 1800 melanoma patients treated with ipilimumab 22% are still alive 3 years later. Antibody therapies with anti PD-L1 (e.g. MPDL3280A, Roche), anti PD-1 (e.g. Nivolumab, BMS) are also ongoing.

Another therapeutic approach that is emerging in the field of cancer is oncolytic viruses (Hermiston, 2006, Curr. Opin. Mol. Ther. 8: 322-30). Oncolytic viruses are capable of selective replication in dividing cells (e.g. cancer cell) while leaving non dividing cells (e.g. normal cells) unharmed. As the infected dividing cells are destroyed by lysis, they release new infectious virus particles to infect the surrounding dividing cells. Cancer cells are ideal hosts for many viruses because they have the antiviral interferon pathway inactivated or have mutated tumour suppressor genes that enable viral replication to proceed unhindered (Chernajovsky et al., 2006, British Med. J. 332: 170-2). A number of viruses including adenovirus, reovirus, measles, herpes simplex, Newcastle disease virus and vaccinia have now been clinically tested as oncolytic agents.

Some viruses are naturally oncolytic (such as reovirus and the Seneca valley picornavirus) while others are engineered for tumor selectivity by modifying the viral genome. Such modifications include functional deletions in essential viral genes, the use of tumor- or tissue-specific promoters to control the viral gene expression and tropism modification to redirect virus to the cancer cell surface.

The first oncolytic virus to be approved by a regulatory agency was a genetically modified adenovirus named H101 (Shanghai Sunway Biotech) that gained approval in 2005 from China's State Food and Drug Administration (SFDA) for the treatment of head and neck cancer. Another oncolytic adenovirus, named ONYX-015 is in ongoing clinical trials for the treatment of various solid tumors (in phase III for the treatment of recurrent head and neck cancer) (Cohen et al., 2001, Curr. Opin. Investig. Drugs 2: 1770-5). As another example, oncolytic herpes simplex 1 (T-VEC) was genetically engineered to attenuate the virus virulence, increase selectivity for cancer cells and enhance antitumor immune response (through GM-CSF expression). Clinical efficacy in unresectable melanoma has been demonstrated in Phase II and Phase III clinical trials (Senzer et al, 2009, J. Clin. Oncol. 27: 5763-71).

Vaccinia viruses (VV) possess many of the key attributes necessary for use in oncolytic virotherapy such as natural tropism for tumors, strong lytic ability, short life cycle with rapid cell-to-cell spread, highly efficient gene expression and a large cloning capacity. In addition, they have been delivered to millions of individuals during the smallpox eradication campaign without major safety concerns. In this respect, a TK and VGF double deleted VV (Wyeth strain) expressing GM-CSF (named JX-963) showed significant cancer selectivity in tumor bearing mice (Thorne et al., 2007, J Clin Invest. 117: 3350-8). On the same line, JX-594, a TK-deleted VV (Wyeth strain) armed with GM-CSF, has shown promising clinical data, and a randomized Phase III trial in hepatocellular carcinoma is expected to start soon.

Combination therapies involving oncolytic virus and immune checkpoint inhibitors have been described in the literature. WO2014/022138 describes the combination of irradiated tumor cells, an oncolytic adenovirus and an anti CTLA4 antibody for use for treating bladder or prostate cancer. WO2014/047350 envisages a recombinant oncolytic virus with a gene encoding an anti-PD-1 antibody inserted in the viral genome without providing any working example that would support utility of such an oncolytic virus.

Technical Problem

One may expect that cancer will continue to be a serious global health threat for many years due to the high number of causal factors that may act together or separately to initiate or promote the development of a cancer. Moreover, malignant and especially metastatic tumors are often resistant to conventional therapies explaining the significant morbidity of some cancers.

Thus, there is an important need to develop more effective approaches, for improving prevention and treatment of such proliferative diseases, and especially metastatic cancers. The present invention provides a unique product combining oncolysis for killing dividing cells and immune checkpoint for breaking cancer-associated immune tolerance.

This technical problem is solved by the provision of the embodiments as defined in the claims.

Other and further aspects, features and advantages of the present invention will be apparent from the following description of the presently preferred embodiments of the invention. These embodiments are given for the purpose of disclosure.

SUMMARY OF THE INVENTION

The present invention concerns an oncolytic virus comprising inserted in its genome one or more nucleic acid molecule(s) encoding one or more immune checkpoint modulator(s).

The oncolytic virus is preferably selected from the group consisting of reovirus, New Castle Disease virus (NDV), vesicular stomatitis virus (VSV), measles virus, influenza virus, Sinbis virus, adenovirus, poxvirus and herpes virus (HSV) and the like. In one embodiment, the oncolytic virus is a vaccinia virus. In a preferred embodiment, the vaccinia virus is engineered to lack thymidine kinase activity (e.g. the genome of said VV has an inactivating mutation in J2R gene to produce a defective TK phenotype). Alternatively or in combination, the vaccinia virus is engineered to lack RR activity (e.g. the genome of said VV has an inactivating mutation in 14L and/or F4L gene to produce a defective RR phenotype).

In one embodiment, the vaccinia virus further expresses at least one therapeutic gene, in particular a gene encoding a suicide gene product and/or an immunostimulatory protein.

In one embodiment, the encoded one or more immune checkpoint modulator(s) is an antagonist molecule that antagonizes the activity of PD-1, PD-L1 or CTLA4 with a specific preference for an anti PD-1 antibody and/or an anti CTLA4 antibody.

The present invention further provides a composition comprising said oncolytic virus, eventually with a pharmaceutical acceptable vehicle. In one embodiment, the composition is formulated for intravenous or intratumoral administration.

The present invention also concerns the use of said oncolytic virus or composition thereof for treating a proliferative disease as well as a method of treatment relying on the administration of an effective amount of said oncolytic virus or composition thereof. In one embodiment, the proliferative disease treated by the method of the invention is cancer and especially melanoma, renal cancer, prostate cancer, breast cancer, colorectal cancer, lung cancer and liver cancer. In one embodiment, the use or method comprises an additional step in which a pharmaceutically acceptable amount of a prodrug is administered to said mammal. The administration of said prodrug takes place preferably at least 3 days after the administration of said oncolytic virus or virus composition.

DETAILED DESCRIPTION

The present invention concerns an oncolytic virus comprising inserted in its genome one or more nucleic acid molecule(s) encoding one or more immune checkpoint modulator(s).

Definitions

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "one or more" refers to either one or a number above one (e.g. 2, 3, 4, 5, etc.).

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

As used herein, when used to define products, compositions and methods, the term "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are open-ended and do not exclude additional, unrecited elements or method steps. Thus, a polypeptide "comprises" an amino acid sequence when the amino acid sequence might be part of the final amino acid sequence of the polypeptide. Such a polypeptide can have up to several hundred additional amino acids residues. "Consisting essentially of" means excluding other components or steps of any essential significance. Thus, a composition consisting essentially of the recited components would not exclude trace contaminants and pharmaceutically acceptable carriers. A polypeptide "consists essentially of" an amino acid sequence when such an amino acid sequence is present with eventually only a few additional amino acid residues. "Consisting of" means excluding more than trace elements of other components or steps. For example, a polypeptide "consists of" an amino acid sequence when the polypeptide does not contain any amino acids but the recited amino acid sequence.

The terms "polypeptide", "peptide" and "protein" refer to polymers of amino acid residues which comprise at least nine or more amino acids bonded via peptide bonds. The polymer can be linear, branched or cyclic and may comprise naturally occurring and/or amino acid analogs and it may be interrupted by non-amino acids. As a general indication, if the amino acid polymer is more than 50 amino acid residues, it is preferably referred to as a polypeptide or a protein whereas if it is 50 amino acids long or less, it is referred to as a "peptide".

Within the context of the present invention, the terms "nucleic acid", "nucleic acid molecule", "polynucleotide" and "nucleotide sequence" are used interchangeably and define a polymer of any length of either polydeoxyribonucleotides (DNA) (e.g. cDNA, genomic DNA, plasmids, vectors, viral genomes, isolated DNA, probes, primers and any mixture thereof) or polyribonucleotides (RNA) (e.g. mRNA, antisense RNA, SiRNA) or mixed polyribo-polydeoxyribonucleotides. They encompass single or double-stranded, linear or circular, natural or synthetic, modified or unmodified polynucleotides. Moreover, a polynucleotide may comprise non-naturally occurring nucleotides and may be interrupted by non-nucleotide components.

The term "analog" or "variant" as used herein refers to a molecule (polypeptide or nucleic acid) exhibiting one or more modification(s) with respect to the native counterpart. Any modification(s) can be envisaged, including substitution, insertion and/or deletion of one or more nucleotide/amino acid residue(s). Preferred are analogs that retain a degree of sequence identity of at least 80%, preferably at least 85%, more preferably at least 90%, and even more preferably at least 98% identity with the sequence of the native counterpart.

In a general manner, the term "identity" refers to an amino acid to amino acid or nucleotide to nucleotide correspondence between two polypeptide or nucleic acid sequences. The percentage of identity between two sequences is a function of the number of identical positions shared by the sequences, taking into account the number of gaps which need to be introduced for optimal alignment and the length of each gap. Various computer programs and mathematical algorithms are available in the art to determine the percentage of identity between amino acid sequences, such as for example the Blast program available at NCBI or ALIGN in Atlas of Protein Sequence and Structure (Dayhoffed, 1981, Suppl., 3: 482-9). Programs for determining identity between nucleotide sequences are also available in specialized data base (e.g. Genbank, the Wisconsin Sequence Analysis Package, BESTFIT, FASTA and GAP programs). For illustrative purposes, "at least 80% identity" means 80%, 81%, 82%, 83%, 84%, 85%, 86%, 87%, 88%, 89%, 90%, 91%, 92%, 93%, 94%, 95%, 96%, 97%, 98%, 99% or 100%.

As used herein, the term "isolated" refers to a protein, polypeptide, peptide, polynucleotide, vector, etc., that is removed from its natural environment (i.e. separated from at least one other component(s) with which it is naturally associated or found in nature). For example, a nucleotide sequence is isolated when it is separated of sequences normally associated with it in nature (e.g. dissociated from a genome) but it can be associated with heterologous sequences.

The term "obtained from", "originating" or "originate" is used to identify the original source of a component (e.g. polypeptide, nucleic acid molecule) but is not meant to limit the method by which the component is made which can be, for example, by chemical synthesis or recombinant means.

As used herein, the term "host cell" should be understood broadly without any limitation concerning particular organization in tissue, organ, or isolated cells. Such cells may be of a unique type of cells or a group of different types of cells such as cultured cell lines, primary cells and dividing cells. In the context of the invention, the term "host cells" include prokaryotic cells, lower eukaryotic cells such as yeast, and other eukaryotic cells such as insect cells, plant and mammalian (e.g. human or non-human) cells as well as cells capable of producing the oncolytic virus and/or the immune checkpoint modulator(s) for use in the invention. This term also includes cells which can be or has been the recipient of the vectors described herein as well as progeny of such cells.

As used herein, the term "oncolytic virus" refers to a virus capable of selectively replicating in dividing cells (e.g. a proliferative cell such as a cancer cell) with the aim of slowing the growth and/or lysing said dividing cell, either in vitro or in vivo, while showing no or minimal replication in non-dividing cells. Typically, an oncolytic virus contains a viral genome packaged into a viral particle (or virion) and is infectious (i.e. capable of infecting and entering into a host cell or subject). As used herein, this term encompasses DNA or RNA vector (depending on the virus in question) as well as viral particles generated thereof.

The term "treatment" (and any form of treatment such as "treating", "treat") as used herein encompasses prophylaxis (e.g. preventive measure in a subject at risk of having the pathological condition to be treated) and/or therapy (e.g. in a subject diagnosed as having the pathological condition), eventually in association with conventional therapeutic modalities. The result of the treatment is to slow down, cure, ameliorate or control the progression of the targeted pathological condition. For example, a subject is successfully treated for a cancer if after administration of an oncolytic virus as described herein, the subject shows an observable improvement of its clinical status.

The term "administering" (or any form of administration such as "administered") as used herein refers to the delivery to a subject of a therapeutic agent such as the oncolytic virus described herein.

As used herein, the term "proliferative disease" encompasses any disease or condition resulting from uncontrolled cell growth and spread including cancers as well as diseases associated to an increased osteoclast activity (e.g. rheumatoid arthritis, osteoporosis, etc.) and cardiovascular diseases (restenosis that results from the proliferation of the smooth muscle cells of the blood vessel wall, etc.). The term "cancer" may be used interchangeably with any of the terms "tumor", "malignancy", "neoplasm", etc. These terms are meant to include any type of tissue, organ or cell, any stage of malignancy (e.g. from a prelesion to stage IV)

The term "subject" generally refers to an organism for whom any product and method of the invention is needed or may be beneficial. Typically, the organism is a mammal, particularly a mammal selected from the group consisting of domestic animals, farm animals, sport animals, and primates. Preferably, the subject is a human who has been diagnosed as having or at risk of having a proliferative disease such as a cancer. The terms "subject" and "patients" may be used interchangeably when referring to a human organism and encompasses male and female. The subject to be treated may be a newborn, an infant, a young adult or an adult.

The term "combination" or "association" as used herein refers to any arrangement possible of various components (e.g. an oncolytic virus and one or more substance effective in anticancer therapy). Such an arrangement includes mixture of said components as well as separate combinations for concomitant or sequential administrations. The present invention encompasses combinations comprising equal molar concentrations of each component as well as combinations with very different concentrations. It is appreciated that optimal concentration of each component of the combination can be determined by the artisan skilled in the art.

The term "immune checkpoint modulator" refers to a molecule capable of modulating the function of an immune checkpoint protein in a positive or negative way (in particular the interaction between an antigen presenting cell (APC) or a cancer cell and a T effector cell). The term "immune checkpoint" refers to a protein directly or indirectly involved in an immune pathway that under normal physiological conditions is crucial for preventing uncontrolled immune reactions and thus for the maintenance of self-tolerance and/or tissue protection. The one or more immune checkpoint modulator(s) in use herein may independently act at any step of the T cell-mediated immunity including clonal selection of antigen-specific cells, T cell activation, proliferation, trafficking to sites of antigen and inflammation, execution of direct effector function and signaling through cytokines and membrane ligands. Each of these steps is regulated by counterbalancing stimulatory and inhibitory signals that in fine tune the response. In the context of the present invention, the term encompasses immune checkpoint modulator(s) capable of down-regulating at least partially the function of an inhibitory immune checkpoint (antagonist) and/or immune checkpoint modulator(s) capable of up-regulating at least partially the function of a stimulatory immune checkpoint (agonist).

Oncolytic Virus

The oncolytic virus of the present invention can be obtained from any member of virus identified at present time provided that it is oncolytic by its propensity to selectivity replicate and kill dividing cells as compared to non-dividing cells. It may be a native virus that is naturally oncolytic or may be engineered by modifying one or more viral genes so as to increase tumor selectivity and/or preferential replication in dividing cells, such as those involved in DNA replication, nucleic acid metabolism, host tropism, surface attachment, virulence, lysis and spread (see for example Kirn et al., 2001, Nat. Med. 7: 781; Wong et al., 2010, Viruses 2: 78-106). One may also envisage placing one or more viral gene(s) under the control of event or tissue-specific regulatory elements (e.g. promoter).

Exemplary oncolytic viruses include without limitation reovirus, Seneca Valley virus (SVV), vesicular stomatitis virus (VSV), Newcastle disease virus (NDV), herpes simplex virus (HSV), morbillivirus virus, retrovirus, influenza virus, Sin bis virus, poxvirus, adenovirus, or the like.

In one embodiment, the oncolytic virus of the present invention is obtained from a reovirus. A representative example includes Reolysin (under development by Oncolytics Biotech; NCT01166542).

In one embodiment, the oncolytic virus of the present invention is obtained from a Seneca Valley virus. A representative example includes NTX-010 (Rudin et al., 2011, Clin. Cancer. Res. 17(4): 888-95).

In one embodiment, the oncolytic virus of the present invention is obtained from a vesicular stomatitis virus (VSV). Representative examples are described in the literature (e.g. Stojdl et al., 2000, Nat. Med. 6(7): 821-5; Stojdl et al., 2003, Cancer Cell 4(4): 263-75).

In one embodiment, the oncolytic virus of the present invention is obtained from a Newcastle disease virus. Representative examples include without limitation the 73-T PV701 and HDV-HUJ strains as well as those described in the literature (e.g. Phuangsab et al., 2001, Cancer Lett. 172(1): 27-36; Lorence et al., 2007, Curr. Cancer Drug Targets 7(2): 157-67; Freeman et al., 2006, Mol. Ther. 13(1): 221-8).

In one embodiment, the oncolytic virus of the present invention is obtained from a herpes virus. The Herpesviridae are a large family of DNA viruses that all share a common structure and are composed of relatively large double-stranded, linear DNA genomes encoding 100-200 genes encapsided within an icosahedral capsid which is enveloped in a lipid bilayer membrane. Although the oncolytic herpes virus can be derived from different types of HSV, particularly preferred are HSV1 and HSV2. The herpes virus may be genetically modified so as to restrict viral replication in tumors or reduce its cytotoxicity in non-dividing cells. For example, any viral gene involved in nucleic acid metabolism may be inactivated, such as thymidine kinase (Martuza et al., 1991, Science 252: 854-6), ribonucleotide reductase (RR) (Boviatsis et al., Gene Ther. 1: 323-31; Mineta et al., 1994, Cancer Res. 54: 3363-66), or uracil-N-glycosylase (Pyles et al., 1994, J. Virol. 68: 4963-72). Another aspect involves viral mutants with defects in the function of genes encoding virulence factors such as the ICP34.5 gene (Chambers et al., 1995, Proc. Natl. Acad. Sci. USA 92: 1411-5). Representative examples of oncolytic herpes virus include NV1020 (e.g. Geevarghese et al., 2010, Hum. Gene Ther. 21(9): 1119-28) and T-VEC (Andtbacka et al., 2013, J. Clin. Oncol. 31, abstract number LBA9008).

In one embodiment, the oncolytic virus of the present invention is obtained from a morbillivirus which can be obtained from the paramyxoviridae family, with a specific preference for measles virus. Representative examples of oncolytic measles viruses include without limitation MV-Edm (McDonald et al., 2006; Breast Cancer Treat. 99(2): 177-84) and HMWMAA (Kaufmann et al., 2013, J. Invest. Dermatol. 133(4): 1034-42)

In one embodiment, the oncolytic virus of the present invention is obtained from an adenovirus. Methods are available in the art to engineer oncolytic adenoviruses. An advantageous strategy includes the replacement of viral promoters with tumor-selective promoters or modifications of the E1 adenoviral gene product(s) to inactivate its/their binding function with p53 or retinoblastoma (Rb) protein that are altered in tumor cells. In the natural context, adenovirus E1B55kDa gene cooperates with another adenoviral product to inactivate p53 (p53 is frequently dysregulated in cancer cells), thus preventing apoptosis. Representative examples of oncolytic adenovirus include ONYX-015 (e.g. Khuri et al., 2000, Nat. Med 6(8): 879-85) and H101 also named Oncorine (Xia et al., 2004, Ai Zheng 23(12): 1666-70).

In one embodiment, the oncolytic virus of the present invention is a poxvirus. As used herein the term "poxvirus" refers to a virus belonging to the Poxviridae family, with a specific preference for a poxvirus belonging to the Chordopoxviridae subfamily and more preferably to the Orthopoxvirus genus. Sequences of the genome of various poxviruses, for example, the vaccinia virus, cowpox virus, Canarypox virus, Ectromelia virus, Myxoma virus genomes are available in the art and specialized databases such as Genbank (accession number NC_006998, NC_003663, NC_005309, NC_004105, NC_001132 respectively).

Desirably, the oncolytic poxvirus is an oncolytic vaccinia virus. Vaccinia viruses are members of the poxvirus family characterized by a 200kb double-stranded DNA genome that encodes numerous viral enzymes and factors that enable the virus to replicate independently from the host cell machinery. The majority of vaccinia virus particles is intracellular (IMV for intracellular mature virion) with a single lipid envelop and remains in the cytosol of infected cells until lysis. The other infectious form is a double enveloped particle (EEV for extracellular enveloped virion) that buds out from the infected cell without lysing it.

Although it can derive from any vaccinia virus strain, Elstree, Wyeth, Copenhagen and Western Reserve strains are particularly preferred. The gene nomenclature used herein is that of Copenhagen vaccinia strain. It is also used herein for the homologous genes of other poxviridae unless otherwise indicated. However, gene nomenclature may be different according to the pox strain but correspondence between Copenhagen and other vaccinia strains are generally available in the literature.

Preferably, the oncolytic vaccinia virus of the present invention is modified by altering for one or more viral gene(s). Said modification(s) preferably lead(s) to the synthesis of a defective protein unable to ensure the activity of the protein produced under normal conditions by the unmodified gene (or lack of synthesis). Modifications encompass deletion, mutation and/or substitution of one or more nucleotide(s) (contiguous or not) within the viral gene or its regulatory elements. Modification(s) can be made in a number of ways known to those skilled in the art using conventional recombinant techniques. Exemplary modifications are disclosed in the literature with a specific preference for those altering viral genes involved in DNA metabolism, host virulence, IFN pathway (see e.g. Guse et al., 2011, Expert Opinion Biol. Ther.11(5): 595-608) and the like.

More preferably, the oncolytic poxvirus of the present invention is modified by altering the thymidine kinase-encoding gene (locus J2R). The TK enzyme is involved in the synthesis of deoxyribonucleotides. TK is needed for viral replication in normal cells as these cells have generally low concentration of nucleotides whereas it is dispensable in dividing cells which contain high nucleotide concentration.

Alternatively or in combination, the oncolytic poxvirus of the present invention is modified by altering at least one gene or both genes encoding Ribonucleotide reductase (RR). In the natural context, this enzyme catalyzes the reduction of ribonucleotides to deoxyribonucleotides that represents a crucial step in DNA biosynthesis. The viral enzyme is similar in subunit structure to the mammalian enzyme, being composed of two heterologous subunits, designed R1 and R2 encoded respectively by the 14L and F4L locus. Sequences for the 14L and F4L genes and their locations in the genome of various poxvirus are available in public databases, for example via accession number DQ437594, DQ437593, DQ377804, AH015635, AY313847, AY313848, NC_003391, NC_003389, NC_003310, M-35027, AY243312, DQ011157, DQ011156, DQ011155, DQ011154, DQ011153, Y16780, X71982, AF438165, U60315, AF410153, AF380138, U86916, L22579, NC_006998, DQ121394 and NC_008291. In the context of the invention, either the 14L gene (encoding the R1 large subunit) or the F4L gene (encoding the R2 small subunit) or both may be inactivated.

Alternatively or in combination, other strategies may also be pursued to further increase the virus tumor-specificity. A representative example of suitable modification includes disruption of the VGF-encoding gene from the viral genome. VGF (for VV growth factor) is a secreted protein which is expressed early after cell infection and its function seems important for virus spread in normal cells. Another example is the disruption of the A56R gene coding for hemagglutinin, eventually in combination with TK deletion (Zhang et al., 2007, Cancer Res. 67: 10038-46). Disruption of interferon modulating gene(s) may also be advantageous (e.g. the B8R or B18R gene) or the caspase-1 inhibitor B13R gene. Another suitable modification comprises the disruption of the F2L gene which encodes the viral dUTPase involved in both maintaining the fidelity of DNA replication and providing the precursor for the production of TMP by thymidylate synthase (Broyles et al., 1993, Virol. 195: 863-5). Sequence of the vaccinia virus F2L gene is available in genbank via accession number M25392.

In a preferred embodiment, the oncolytic virus of this invention is a vaccinia virus defective for TK resulting from inactivating mutations in the J2R gene. In another preferred embodiment, the oncolytic virus of this invention is a vaccinia virus defective for both TK and RR activities resulting from inactivating mutations in both the J2R gene and the 14L and/or F4L gene(s) carried by the viral genome (e.g. as described in WO2009/065546 and Foloppe et al., 2008, Gene Ther., 15: 1361-71). In another preferred embodiment, the oncolytic virus of this invention is a vaccinia virus defective for dUTPase resulting from inactivating mutations in the F2L gene (e.g. as described in WO2009/065547), eventually in combination with disruption of at least one of TK and RR activities or both (resulting in a virus with inactivating mutations in the F2L; F2L and J2R gene; F2L and 14L; or F2L, J2R and 14L).

Therapeutic Genes

In one embodiment, the oncolytic virus of this invention further expresses at least one therapeutic gene inserted in the viral genome. A "therapeutic gene" encodes a product capable of providing a biological activity when administered appropriately to a subject, which is expected to cause a beneficial effect on the course or a symptom of the pathological condition to be treated by either potentiating anti-tumor efficacy or reinforcing the oncolytic nature of the virus. In the context of the invention, the therapeutic gene can be of mammal origin (e.g. human, murine, rabbit, etc.) or not (e.g. of bacterial, yeast or viral origin).

A vast number of therapeutic genes may be envisaged in the context of the invention such as those encoding polypeptides that can compensate for defective or deficient proteins in the subject, or those that act through toxic effects to limit or remove harmful cells from the body or those that encode immunity conferring polypeptides. They may be native genes or genes obtained from the latter by mutation, deletion, substitution and/or addition of one or more nucleotides. Advantageously, the oncolytic virus of the present invention carries a therapeutic gene selected from the group consisting of genes encoding suicide gene products and immunostimulatory proteins.

Suicide Gene

The term "suicide gene" refers to a gene coding for a protein able to convert a precursor of a drug into a cytoxic compound. Suicide genes comprise but are not limited to genes coding protein having a cytosine deaminase activity, a thymidine kinase activity, an uracil phosphoribosyl transferase activity, a purine nucleoside phosphorylase activity and a thymidylate kinase activity. Examples of suicide genes and corresponding precursors of a drug comprising one nucleobase moiety are disclosed in the following table

TABLE 1

| Suicide gene | prodrug |
| --- | --- |
| Thymidine Kinase | Ganciclovir; Ganciclovir elaidic acid ester; penciclovir; Acyclovir; Valacyclovir; (E)-5-(2-bromovinyl)-2'-deoxyuridine; zidovudine; 2'-Exo-methanocarbathymidine |
| Cytosine deaminase | 5-Fluorocytosine |
| Purine nucleoside phosphorylase | 6-Methylpurine deoxyriboside; Fludarabine |
| uracil phosphoribosyl transferase | 5-Fluorocytosine; 5-Fluorouracil |
| thymidylate kinase. | Azidothymidine |

Desirably, the suicide gene encodes a protein having at least a CDase activity. In the prokaryotes and lower eukaryotes (it is not present in mammals), CDase is involved in the pyrimidine metabolic pathway by which exogenous cytosine is transformed into uracil by means of a hydrolytic deamination. CDase also deaminates an analogue of cytosine, i.e. 5-fluorocytosine (5-FC), thereby forming 5-fluorouracil (5-FU), a compound which is highly cytotoxic when it is converted into 5-fluoro-UMP (5-FUMP). CDase encoding nucleic acid molecule can be obtained from any prokaryotes and lower eukaryotes such as *Saccharomyces cerevisiae* (FCY1 gene), *Candida Albicans* (FCA1 gene) and *Escherichia coli* (codA gene). The gene sequences and encoded CDase proteins have been published and are available in specialized data banks (SWISSPROT EMBL, Genbank, Medline and the like). Functional analogues of these genes may also be used. Such analogues preferably have a nucleic acid sequence having a degree of identity of at least 70%, advantageously of at least 80%, preferably of at least 90%, and most preferably of at least 95% with the nucleic acid sequence of the native gene.

Alternatively or in combination, the oncolytic virus of the invention carries in its viral genome a suicide gene encoding a polypeptide having uracil phosphoribosyl transferase (UPRTase) activity. In prokaryotes and lower eukaryotes, uracil is transformed into UMP by the action of UPRTase. This enzyme converts 5-FU into 5-FUMP. By way of illustration, the nucleic acid sequences encoding the UPRTases from *E. coli* (Andersen et al., 1992, European J. Biochem. 204: 51-56), from *Lactococcus lactis* (Martinussen et al., 1994, J. Bacteriol. 176: 6457-63), from *Mycobacterium bovis* (Kim et al., 1997, Biochem. Mol. Biol. Internat. 41: 1117-24) and from *Bacillus subtilis* (Martinussen et al., 1995, J. Bacteriol. 177: 271-4) may be used in the context of the invention. However, it is most particularly preferred to use a yeast UPRTase and in particular that encoded by the *S. cerevisiae* (FUR1 gene) whose sequence is disclosed in Kern et al. (1990, Gene 88: 149-57). Functional UPRTase analogues may also be used such as the N-terminally truncated FUR1 mutant described in EP998568 (with a deletion of the 35 first residues up to the second Met residue present at position 36 in the native protein) which exhibits a higher UPRTase activity than that of the native enzyme.

Preferably, the suicide gene inserted in the viral genome of the oncolytic virus of the present invention encodes a polypeptide having CDase and UPRTase activities. Such a polypeptide can be engineered by fusion of two enzymatic domains, one having the CDase activity and the second having the UPRTase activity. Exemplary polypeptides include without limitation fusion polypeptides codA::upp, FCY1::FUR1 and FCY1::FUR1[Delta] 105 (FCU1) and FCU1-8 described in WO96/16183, EP998568 and WO2005/07857. Of particular interest is the FCU1 suicide gene (or FCY1::FUR1[Delta] 105 fusion) encoding a polypeptide comprising the amino acid sequence represented in the sequence identifier SEQ ID NO: 1 of WO2009/065546. The present invention encompasses analogs of such polypeptides providing they retain the CDase, and/or UPRTase activities. It is within the reach of the skilled person to isolate the CDase and/or UPRTase—encoding nucleic acid molecules from the published data, eventually engineer analogs thereof and test the enzymatic activity in an acellular or cellular system according to conventional techniques (see e.g. EP998568).

Immunostimulatory Therapeutic Genes

As used herein, the term "immunostimulatory protein" refers to a protein which has the ability to stimulate the immune system, in a specific or non-specific way. A vast number of proteins are known in the art for their ability to exert an immunostimulatory effect. Examples of suitable immunostimulatory proteins in the context of the invention include without limitation cytokines, with a specific preference for interleukins (e.g. IL-2, IL-6, IL-12, IL-15, IL-24), chemokines (e.g. CXCL10, CXCL9, CXCL11), interferons (e.g. IFNg, IFNalpha), tumor necrosis factor (TNF), colony-stimulating factors (e.g. GM-CSF, C-CSF, M-CSF . . . ), APC (for Antigen Presenting Cell)-exposed proteins (e.g. B7.1, B7.2 and the like), growth factors (Transforming Growth Factor TGF, Fibroblast Growth Factor FGF, Vascular Endothelial Growth Factors VEGF, and the like), MHC antigens of class I or II, apoptosis inducers or inhibitors (e.g. Bax, Bcl2, BclX . . . ), cytostatic agents (p21, p16, Rb . . . ), immunotoxins, antigenic polypeptides (antigenic polypeptides, epitopes, and the like) and markers (beta-galactosidase, luciferase . . . ). Preferably, the imunostimulatory protein is an interleukin or a colony-stimulating factor, with a specific preference for GM-CSF.

Immune Checkpoint Modulator(s)

Immune checkpoints and modulators thereof as well as methods of using such compounds are described in the literature. In accordance with this invention, the one or more immune checkpoint modulator(s) may independently be a polypeptide comprising a domain capable of binding the targeted immune checkpoint and/or inhibiting the binding of a ligand to said targeted immune checkpoint so as to exert an antagonist function (i.e. being capable of antagonizing an immune checkpoint-mediated inhibitory signal) or an agonist function (i.e. being capable of boosting an immune checkpoint-mediated stimulatory signal). Such one or more immune checkpoint modulator(s) can be independently selected from the group consisting of peptides (e.g. peptide ligands), soluble domains of natural receptors, RNAi, antisense molecules, antibodies and protein scaffolds.

In a preferred embodiment, the immune checkpoint modulator is an antibody. In the context of the invention, "antibody" ("Ab") is used in the broadest sense and encompasses naturally occurring and engineered by man as well as full length antibodies or functional fragments or analogs thereof that are capable of binding the target immune checkpoint or epitope (thus retaining the target-binding portion). The antibody encoded by the oncolytic virus of the invention can be of any origin, e.g. human, humanized, animal (e.g. rodent or camelid antibody) or chimeric. It may be of any isotype (e.g. IgG1, IgG2, IgG3, IgG4, IgM isotype, etc.). In addition, it may be glycosylated, partially glycosylated or non-glycosylated (e.g. by mutating one or more residue(s) within the site(s) of glycosylation). The term antibody also includes bispecific or multispecific antibodies so long as they exhibit the binding specificity described herein.

For illustrative purposes, full length antibodies are glycoproteins comprising at least two heavy (H) chains and two light (L) chains inter-connected by disulfide bonds. Each heavy chain is comprised of a heavy chain variable region (VH) and a heavy chain constant region which is made of three CH1, CH2 and CH3 domains (eventually with a hinge between CH1 and CH2). Each light chain is comprised of a light chain variable region (VL) and a light chain constant region which comprises one CL domain. The VH and VL regions comprise hypervariable regions, named complementarity determining regions (CDR), interspersed with more conserved regions named framework regions (FR). Each VH and VL is composed of three CDRs and four FRs in the following order: FR1-CDR1-FR2-CDR2-FR3-CDR3-FR4. The CDR regions of the heavy and light chains are determinant for the binding specificity.

As used herein, a "humanized antibody" refers to a non-human (e.g. murine, camel, rat, etc.) antibody whose protein sequence has been modified to increase its similarity to a human antibody (i.e. produced naturally in humans). The process of humanization is well known in the art (see e.g. Presta et al., 1997, Cancer Res. 57(20): 4593-9; U.S. Pat. Nos. 5,225,539; 5,530,101; 6,180,370; WO2012/110360). For example, the immune checkpoint antibody for use herein can be humanized by substituting one or more residue of the FR regions to look like human immunoglobulin sequence whereas the vast majority of the residues of the variable regions (especially the CDRs) are not modified and correspond to those of a non-human immunoglobulin. For general guidance, the number of these amino acid substitutions in the FR regions is typically no more than 20 in each variable region VH or VL.

As used herein, a "chimeric antibody" refers to an antibody comprising one or more element(s) of one species and one or more element(s) of another species, for example, a non-human antibody comprising at least a portion of a constant region (Fc) of a human immunoglobulin.

Many forms of antibody can be expressed by the oncolytic virus of the invention. Representative examples include without limitation Fab, Fab', F(ab')2, dAb, Fd, Fv, scFv, di-scFv and diabody, etc. More specifically:

(i) a Fab fragment represented by a monovalent fragment consisting of the VL, VH, CL and CH1 domains;
(ii) a F(ab')2 fragment represented by a bivalent fragment comprising two Fab fragments linked by at least one disulfide bridge at the hinge region;
(iii) a Fd fragment consisting of the VH and CH1 domains;
(iv) a Fv fragment consisting of the VL and VH domains of a single arm of an antibody,
(v) a dAb fragment consisting of a single domain variable fragment (VH or VL domain);
(vi) a single chain Fv (scFv) comprising the two domains of a Fv fragment, VL and VH, that are fused together, eventually with a linker to make a single protein chain (see e.g. Bird et al., 1988, Science 242: 423-6; Huston et al., 1988, Proc. Natl. Acad. Sci. USA 85: 5879-83; U.S. Pat. Nos. 4,946,778; 5,258,498); and
(vii) any other artificial antibody.

If needed, such fragments and analogs may be screened for functionality in the same manner as with intact antibodies (e.g. by standard ELISA assay).

In a preferred embodiment, at least one of the one or more immune checkpoint modulator(s) encoded by the oncolytic virus of the present invention is a monoclonal antibody, with a specific preference for a human (in which both the framework regions are derived from human germline immunoglobin sequences) or a humanized antibody according to well-known humanization process.

Desirably, the one or more immune checkpoint modulator(s) encoded by the oncolytic virus of the present invention antagonize(s) at least partially (e.g. more than 50%) the activity of inhibitory immune checkpoint(s), in particular those mediated by any of the following PD-1, PD-L1, PD-L2, LAG3, Tim3, BTLA and CTLA4, with a specific preference for a monoclonal antibody that specifically binds to any of such target proteins. The term "specifically binds to" refers to the capacity to a binding specificity and affinity for a particular target or epitope even in the presence of a heterogeneous population of other proteins and biologics. Thus, under designated assay conditions, the antibody in use in the invention binds preferentially to its target and does not bind in a significant amount to other components present in a test sample or subject. Preferably, such an antibody shows high affinity binding to its target with an equilibrium dissociation constant equal or below $1\times10^{-6}$M (e.g. at least $0.5\times10^{-6}$, $1\times10^{-7}$, $1\times10^{-8}$, $1\times10^{-9}$, $1\times10^{-10}$, etc.). Alternatively, the encoded one or more immune checkpoint modulator(s) exert(s) an agonist function in the sense that it is capable of stimulating or reinforcing stimulatory signals, in particular those mediated by CD28 with a specific preference for any of ICOS, CD137 (4-1BB), OX40, CD27, CD40, GITR immune checkpoints. Standard assays to evaluate the binding ability of the antibodies toward immune checkpoints are known in the art, including for example, ELISAs, Western blots, RIAs and flow cytometry. The binding kinetics (e.g., binding affinity) of the antibodies also can be assessed by standard assays known in the art, such as by Biacore analysis.

In a preferred embodiment, at least one of the one or more encoded checkpoint modulator(s) is a human or a humanized antibody capable of antagonizing an immune checkpoint involved in T cell-mediated response. A preferred example of immune checkpoint modulator is represented by a modulator capable of antagonizing at least partially the protein Programmed Death 1 (PD-1), and especially an antibody that specifically binds to human PD-1. PD-1 is part of the immunoglobulin (Ig) gene superfamily and a member of the CD28 family. It is a 55 kDa type 1 transmembrane protein expressed on antigen-experienced cells (e.g. activated B cells, T cells, and myeloid cells) (Agata et al., 1996, Int. Immunol. 8: 765-72; Okazaki et al., 2002, Curr. Opin. Immunol. 14: 391779-82; Bennett et al., 2003, J. Immunol 170: 711-8). In normal context, it acts by limiting the activity of T cells at the time of inflammatory response, thereby protecting normal tissues from destruction (Topalian, 2012, Curr. Opin. Immunol. 24: 207-12). Two ligands have been identified for PD-1, respectively PD-L1 (programmed death ligand 1) and PD-L2 (programmed death ligand 2) (Freeman et al., 2000, J. Exp. Med. 192: 1027-34; Carter et al., 2002, Eur. J. Immunol. 32: 634-43). PD-L1 was identified in 20-50% of human cancers (Dong et al., 2002, Nat. Med. 8: 787-9). The interaction between PD-1 and PD-L1 resulted in a decrease in tumor infiltrating lymphocytes, a decrease in T-cell receptor mediated proliferation, and immune evasion by the cancerous cells (Dong et al., 2003, J. Mol. Med. 81: 281-7; Blank et al., 2005, Cancer Immunol. Immunother. 54: 307-314). The complete nucleotide and amino acid PD-1 sequences can be found under GenBank Accession No U64863 and NP_005009.2. A number of anti PD1 antibodies are available in the art (see e.g. those described in WO2004/004771; WO2004/056875; WO2006/121168; WO2008/156712; WO2009/014708; WO2009/114335; WO2013/043569; and WO2014/047350). Preferably, the oncolytic virus of the present invention encodes and expresses an anti PD-1 antibody that is FDA approved or under advanced clinical development such as the ones marketed or developed under the names of Nivolumab (also termed BMS-936558 under development by Bristol Myer Squibb), Pembrolizumab (also termed MK-3475 under development by Merck), and Pidilizumab (also termed CT-011 under development by CureTech). The corresponding nucleotide sequences can be cloned or isolated according to standard techniques based on the information disclosed in the available literature.

Another preferred example of immune checkpoint modulator suitable for expression by the oncolytic virus of the invention is represented by a modulator capable of antagonizing at least partially the PD-1 ligand termed PD-L1, and especially an antibody that recognizes human PD-L1. A number of anti PD-L1 antibodies are available in the art (see e.g. those described in EP1907000). Preferred anti PD-L1 antibodies are FDA approved or under advanced clinical development (MPDL3280A under development by Genentech/Roche and BMS-936559 under development by Bristol Myer Squibb as well as anti-PD-L1 Fc fusions (e.g. AMP-224 developed by Medimmune and AstraZeneca).

One may also use an antagonist of the recently identified VISTA protein that was shown to negatively regulate T cell responses (Wang et al., 2011, J. Exp. Med. 208(3): 577-592). VISTA, also designated PD-1H and PD-L3, resembles members of the PD-L1 family,. For example, anti-VISTA antagonists are described in US2013-0177557.

Still another preferred example of suitable immune checkpoint modulator is represented by a modulator capable of antagonizing at least partially the CTLA-4 protein, and especially an antibody that recognizes human CTLA-4. CTLA4 (for cytotoxic T-lymphocyte-associated antigen 4) also known as CD152 was identified in 1987 (Brunet et al., 1987, Nature 328: 267-70) and is encoded by the CTLA4 gene (Dariavach et al., Eur. J. Immunol. 18: 1901-5). CTLA4 is a member of the immunoglobulin superfamily of receptors. It is expressed on the surface of helper T cells where it primarily regulates the amplitude of the early stages of T cell activation. Recent work has suggested that CTLA-4 may function in vivo by capturing and removing B7-1 and B7-2 from the membranes of antigen-presenting cells, thus making these unavailable for triggering of CD28 (Qureshi et al., Science, 2011, 332: 600-3). The complete CTLA-4 nucleic acid sequence can be found under GenBank Accession No LI 5006. A number of anti CTLA-4 antibodies are available in the art (see e.g. those described in U.S. Pat. No. 8,491,895). Preferred anti CTLA-4 antibodies in the context of this invention are FDA approved or under advanced clinical development. One may cite more particularly ipilimumab marketed by Bristol Myer Squibb as Yervoy (see e.g. U.S. Pat. Nos. 6,984,720; 8,017,114), tremelimumab under development by Pfizer (see e.g. U.S. Pat. Nos. 7,109,003 and 8,143,379) and single chain anti-CTLA4 antibodies (see e.g. WO97/20574 and WO2007/123737).

The oncolytic virus of the present invention may also express an immune checkpoint modulator for antagonizing the LAG3 receptor (see e.g. U.S. Pat. No. 5,773,578).

Another example of suitable immune checkpoint modulator is represented by an OX40 agonist such as agonist ligand of OX40 (OX40L) (see e.g. U.S. Pat. Nos. 5,457,035, 7,622,444; WO03/082919) or an antibody directed to the OX40 receptor (see e.g. U.S. Pat. No. 7,291,331 and WO03/106498). Other examples of immune checkpoint modulators are represented by anti-KIR or anti-CD96 antibody targeting the inhibitory receptors harboured by CD8+ T cells and NK cells.

The present invention encompasses an oncolytic virus encoding more than one immune checkpoint modulator. A preferred example includes without limitation expression of an anti-CTLA-4 antibody and an anti-PD-1 antibody.

Expression of the one or more nucleic acid molecule(s) encoding the immune checkpoint modulator(s) and if any of the therapeutic genes inserted into the viral genome.

The immune checkpoint modulator-encoding nucleic acid molecule(s) and the therapeutic gene may be easily obtained by standard molecular biology techniques (e.g. PCR amplification, cDNA cloning, chemical synthesis) using sequence data accessible in the art and the information provided herein. Methods for cloning antibodies, fragments and analogs thereof are known in the art (see e.g. Harlow and Lane, 1988, Antibodies—A laboratory manual; Cold Spring Harbor Laboratory, Cold Spring Harbor N.Y.). For example, the nucleic acid molecule (e.g. cDNA) encoding the light and heavy chains of the antibody or their CDRs may be isolated from the producing hybridoma (see e.g. Kohler and Milstein, 1975, Nature 256: 495-7; Cote et al., 1983, Proc. Natl. Acad. Sci. USA 80: 2026-30; Cole et al. in Monoclonal antibodies and Cancer Therapy; Alan Liss pp77-96), immunoglobulin gene libraries, or from any available source or the nucleotide sequence may be generated by chemical synthesis. Analogs and fragments may be generated using standard techniques of molecular biology.

The nucleic acid molecule(s) encoding the immune checkpoint modulator(s) and eventually the therapeutic gene(s) can independently be inserted at any location of the viral genome, with a specific preference for a non-essential locus. Insertion into the oncolytic virus can be performed by routine molecular biology, e.g. as described in Sambrook et al. (2001, Molecular Cloning-A Laboratory Manual, Cold Spring Harbor Laboratory). Insertion into an adenoviral vector or a poxviral vector can be performed through homologous recombination as described respectively in Chartier et al. (1996, J. Virol. 70: 4805-10) and Paul et al. (2002, Cancer gene Ther. 9: 470-7). For example, TK, RR and F2L genes as well as intergenic regions are particularly appropriate for insertion in oncolytic vaccinia virus and E3 and E4 regions for insertion in oncolytic adenovirus virus.

In addition, the encoding nucleotide sequences can be optimized for providing high level expression in a particular host cell or subject. It has been indeed observed that, the codon usage patterns of organisms are highly non-random and the use of codons may be markedly different between different hosts. For example, the therapeutic gene may be from bacterial or lower eukaryote origin (e.g. the suicide gene), and thus have an inappropriate codon usage pattern for efficient expression in higher eukaryotic cells (e.g. human). Typically, codon optimization is performed by replacing one or more "native" (e.g. bacterial or yeast) codon corresponding to a codon infrequently used in the host organism of interest by one or more codon encoding the same amino acid which is more frequently used. It is not necessary to replace all native codons corresponding to infrequently used codons since increased expression can be achieved even with partial replacement.

Further to optimization of the codon usage, expression in the host cell or subject can further be improved through additional modifications of the nucleotide sequence(s). For example, various modifications may be envisaged so as to prevent clustering of rare, non-optimal codons being present in concentrated areas and/or to suppress or modify "negative" sequence elements which are expected to negatively influence expression levels. Such negative sequence elements include without limitation the regions having very high (>80%) or very low (<30%) GC content; AT-rich or GC-rich sequence stretches; unstable direct or inverted repeat sequences; R A secondary structures; and/or internal cryptic regulatory elements such as internal TATA-boxes, chi-sites, ribosome entry sites, and/or splicing donor/acceptor sites.

In accordance with the present invention, each of the one or more nucleic acid molecule(s) encoding said immune checkpoint modulator(s) as well as the therapeutic gene(s) inserted in the genome of the oncolytic virus of the invention is operably linked to suitable regulatory elements for its expression in a host cell or subject. As used herein, the term "regulatory elements" or "regulatory sequence" refers to any element that allows, contributes or modulates the expression of the encoding nucleic acid molecule(s) in a given host cell or subject, including replication, duplication, transcription, splicing, translation, stability and/or transport of the nucleic acid(s) or its derivative (i.e. m RNA). As used herein, "operably linked" means that the elements being linked are arranged so that they function in concert for their intended purposes. For example, a promoter is operably linked to a nucleic acid molecule if the promoter effects transcription from the transcription initiation to the terminator of said nucleic acid molecule in a permissive host cell.

It will be appreciated by those skilled in the art that the choice of the regulatory sequences can depend on such factors as the nucleic acid molecule itself, the virus into which it is inserted, the host cell or subject, the level of expression desired, etc. The promoter is of special importance. In the context of the invention, it can be constitutive directing expression of the nucleic acid molecule in many types of host cells or specific to certain host cells (e.g. liver-specific regulatory sequences) or regulated in response to specific events or exogenous factors (e.g. by temperature, nutrient additive, hormone, etc.) or according to the phase of a viral cycle (e.g. late or early). One may also use promoters that are repressed during the production step in response to specific events or exogenous factors, in order to optimize virus production and circumvent potential toxicity of the expressed polypeptide(s).

Promoters suitable for constitutive expression in mammalian cells include but are not limited to the cytomegalovirus (CMV) immediate early promoter (U.S. Pat. No. 5,168,062), the RSV promoter, the adenovirus major late promoter, the phosphoglycero kinase (PGK) promoter (Adra et al., 1987, Gene 60: 65-74), the thymidine kinase (TK) promoter of herpes simplex virus (HSV)-1 and the T7 polymerase promoter (WO98/10088). Vaccinia virus promoters are particularly adapted for expression in oncolytic poxviruses. Representative examples include without limitation the vaccinia 7.5K, H5R, 11K7.5 (Erbs et al., 2008, Cancer Gene Ther. 15(1): 18-28), TK, p28, p11, pB2R, pA35R and K1L promoters, as well as synthetic promoters such as those described in Chakrabarti et al. (1997, Biotechniques 23: 1094-7; Hammond et al, 1997, J. Virol Methods 66: 135-8; and Kumar and Boyle, 1990, Virology 179: 151-8) as well as early/late chimeric promoters. Promoters suitable for oncolytic measles viruses include without limitation any promoter directing expression of measles transcription units (Brandler and Tangy, 2008, CIMID 31: 271).

In particular, when the encoded immune checkpoint modulator(s) comprise(s) an antibody and especially a mAb, with a specific preference for an anti-PD1 antibody, expression of the heavy chain or fragment thereof is placed under the control of a promoter that is stronger than the one used for expressing light chain or fragment thereof. In particular, the promoter for use for expressing the heavy component provides at least 10%, at least 15%, at least 20%, at least 25%, or at least 30% more product as compared to expression of said light component. Appropriate promoters for expression can be tested in vitro (e.g. in a suitable cultured cell line) or in vivo (e.g. in a suitable animal model or in the subject). Examples of suitable promoters for expressing the heavy component of said immune checkpoint modulator comprise CMV, RSV and vaccinia virus pH5R and p11K7.5 promoters. Examples of suitable promoters for expressing the light component of said immune checkpoint modulator comprise PGK, beta-actin and vaccinia virus p7.5K and pA35R promoters.

Those skilled in the art will appreciate that the regulatory elements controlling the expression of the nucleic acid molecule(s) inserted into the viral genome may further comprise additional elements for proper initiation, regulation and/or termination of transcription (e.g. polyA transcription termination sequences), mRNA transport (e.g. nuclear localization signal sequences), processing (e.g. splicing signals), and stability (e.g. introns and non-coding 5' and 3' sequences), translation (e.g. an initiator Met, tripartite leader sequences, IRES ribosome binding sites, signal peptides, etc.).

When appropriate, it may be advantageous to include additional regulatory elements to facilitate expression, trafficking and biological activity of at least one of gene inserted into the viral genome of the oncolytic virus of the invention (i.e. the therapeutic gene(s) and/or the one or more immune checkpoint modulator(s)). For example, a signal peptide may be included for facilitating secretion from the infected cell. The signal peptide is typically inserted at the N-terminus of the protein immediately after the Met initiator. The choice of signal peptides is wide and is accessible to persons skilled in the art. One may also envisage addition of a trans-membrane domain to facilitate anchorage of the encoded protein(s) in a suitable membrane (e.g. the plasmic membrane) of the infected cells. The trans-membrane domain is typically inserted at the C-terminus of the protein just before or at close proximity of the STOP codon. A vast variety of trans-membrane domains are available in the art (see e.g. WO99/03885).

As an additional example, a peptide tag (typically a short peptide sequence able to be recognized by available antisera or compounds) may be also be added for following expression, trafficking or purification of the encoded gene product. A vast variety of tag peptides can be used in the context of the invention including, without limitation, PK tag, FLAG octapeptide, MYC tag, HIS tag (usually a stretch of 4 to 10 histidine residues) and e-tag (U.S. Pat. No. 6,686,152). The tag peptide(s) may be independently positioned at the N-terminus of the protein or alternatively at its C-terminus or alternatively internally or at any of these positions when several tags are employed. Tag peptides can be detected by immunodetection assays using anti-tag antibodies.

As another example, the glycosylation can be altered so as to increase biological activity of the encoded gene product (e.g. to increase). Such modifications can be accomplished, for example, by mutating one or more residues within the site(s) of glycosylation. Altered glycosylation patterns may increase the ADCC ability of antibodies and/or their affinity for their target.

Another approach that may be pursued in the context of the present invention is coupling of the gene product encoded by the oncolytic virus of the invention to an external agent such as a cytotoxic agent and/or a labelling agent. As used herein, the term "cytoxic agent" refers to a compound that is directly toxic to cells, preventing their reproduction or growth such as toxins (e. g. an enzymatically active toxin of bacterial, fungal, plant or animal origin, or fragments thereof). As used herein, "a labeling agent" refers to a detectable compound. The labeling agent may be detectable by itself (e.g., radioactive isotope labels or fluorescent labels) or, in the case of an enzymatic label, may catalyze chemical modification of a substrate compound which is detectable. The coupling may be performed by genetic fusion between the gene product (therapeutic gene(s) and/or immune checkpoint modulator(s)) and the external agent.

In a preferred embodiment, the oncolytic virus of the invention is a vaccinia virus (preferably from the Copenhague strain) defective for both TK and RR activities (e.g. resulting from inactivating mutations in both the viral J2R and 14L genes) in the genome of which is inserted a nucleic acid molecule encoding an anti-PD1 antibody. Desirably, the heavy and light chain elements (e.g. heavy and light chains for mAb expression, or variable fragments thereof for Fab and scFv expression) are respectively placed under the transcriptional control of the pH5R and p7.5K vaccinia promoters. Preferably, the anti-PD1-encoding nucleic acid molecule is inserted within TK locus of the viral genome. More preferably, said vaccinia virus is armed with a suicide gene with a special preference for the FCU1 suicide gene described herein. Even more preferably, the suicide gene (e.g. FCU1) is under the transcriptional control of the p11K7.5 vaccinia promoter. Still more preferably, the FCU1 placed under the control of the vaccinia virus promoter is inserted within TK locus of the virus genome.

In an alternative and also preferred embodiment, the oncolytic virus of the invention is a vaccinia virus (preferably from the Wyeth strain) defective for TK activity (resulting from inactivating mutations in the virus J2R gene) in the genome of which is inserted a nucleic acid molecule encoding an anti-PD1 antibody. More preferably, said vaccinia virus is armed with an immunostimulatory therapeutic gene with a special preference for the human GM-CSF gene described herein. Even more preferably, the therapeutic gene (e.g. GM-CSF) is under the transcriptional control of a synthetic early-late promoter vaccinia promoter and is preferably inserted within TK locus.

Typically, the oncolytic virus of the present invention is produced into a suitable host cell line using conventional techniques including culturing the transfected or infected host cell under suitable conditions so as to allow the production of infectious viral particles and recovering the produced infectious viral particles from the culture of said cell and optionally purifying said recovered infectious viral particles. Suitable host cells for production of the oncolytic virus include without limitation human cell lines such as HeLa (ATCC), 293 cells (Graham et al., 1997, J. Gen. Virol. 36: 59-72), HER96, PER-C6 (Fallaux et al., 1998, Human Gene Ther. 9: 1909-17), avian cells such as those described in WO2005/042728, WO2006/108846, WO2008/129058, WO2010/130756, WO2012/001075, etc.), hamster cell lines such as BHK-21 (ATCC CCL-10) as well as primary chicken embryo fibroblasts (CEF) prepared from chicken embryos obtained from fertilized eggs. The oncolytic virus can be at least partially isolated before being used according to the present invention. Various purification steps can be envisaged, including clarification, enzymatic treatment (e.g. benzonase, protease), chromatographic and filtration steps. Appropriate methods are described in the art (e.g. WO2007/147528; WO2008/138533, WO2009/100521, WO2010/130753, WO2013/022764).

Production of Immune Checkpoint Modulator

In one embodiment, the oncolytic virus may also be utilized in the context of the invention for producing by recombinant means the one or more immune checkpoint modulator(s) that it encodes. It may advantageously comprise one or more additional element(s) enabling maintenance, propagation or expression of the nucleic acid molecule encoding the immune checkpoint modulator in a host cell. Such additional elements comprise marker gene(s) in order to facilitate identification and isolation of the producer host cells (e.g. by complementation of a cell auxotrophy or by antibiotic resistance). Suitable marker genes include without limitation dihydrofolate reductase (dhfr) which confers resistance to methotrexate (Wigler et al., 1980, Proc. Natl. Acad. Sci. USA 77: 3567; O'Hare et al., 1981, Proc. Natl. Acad. Sci. USA 78: 1527); gpt which confers resistance to mycophenolic acid (Mulligan and Berg, 1981, Proc. Natl. Acad. Sci. USA 78: 2072); neo which confers resistance to the aminoglycoside G-418 (Colberre-Garapin et al., 1981, J. Mol. Biol. 150: 1); zeo which confers resistance to zeomycin, kana which confers resistance to kanamycin; hygro, which confers resistance to hygromycin (Santerre et al., 1984, Gene 30: 147). Recombinant viruses lacking a functional TK (e.g. resulting from insertion of the nucleic acid molecule encoding the immune checkpoint modulator into the TK locus) may be selected with media containing bromodeoxyuridine (BrdU). Indeed, TK-viruses are insensitive to the BrdU drug whereas the drug interfers with DNA synthesis in TK+viruses. One may also rely on reporter luminescent or colorometric systems, e.g. based on GFP (green fluorescent protein), luciferase and beta-galactosidase.

The methods for recombinantly producing the immune checkpoint modulator are conventional in the art. Typically such methods comprise (a) introducing the oncolytic virus described herein into a suitable producer cell to produce a transfected or infected producer cell, (b) culturing in-vitro said transfected or infected producer cell under conditions suitable for its growth, (c) recovering the one or more immune checkpoint modulator(s) from the cell culture, and (d) optionally, purifying the recovered immune checkpoint modulator(s). In the context of the invention, producer cells are preferably human or non-human eukaryotic cells. Preferred producer cells include without limitation BHK-21 (baby hamster kidney), CV-1 (African monkey kidney cell line), COS (e.g. COS-7) cells, Chinese hamster ovary (CHO) cells, mouse NIH/3T3 cells, mouse NSO myeloma cells, HeLa cells, Vero cells, HEK293 cells and PERC.6 cells and avian cells (e.g. chicken, duck cells as described herein).

The producer cells can be cultured in conventional fermentation bioreactors, flasks, and petri plates. Culturing can be carried out at a temperature, pH and oxygen content appropriate for a given host cell. No attempts to describe in detail the various methods known for the production of proteins in eukaryotic cells will be made here. Production of the immune checkpoint modulator can be intracellular or preferably secreted outside the producer cell (e.g. in the culture medium).

The immune checkpoint modulator can then be purified by well-known purification methods. The conditions and technology used to purify a particular protein will depend on factors such as the expression conditions, net charge, molecular weight, hydrophobicity, hydrophilicity and will be apparent to those having skill in the art. Moreover, the level of purification will depend on the intended use. If necessary, especially when the immune checkpoint modulator is not secreted outside the producer cell or where it is not secreted completely, it can be recovered by standard lysis procedures, including freeze thaw, sonication, mechanical disruption, use of lysing agents and the like. If secreted, it can be recovered directly from the culture medium. Suitable purification techniques include without limitation ammonium sulfate precipitation, acid extraction, gel electrophoresis, filtration and chromatographic methods (e.g. reverse phase, size exclusion, ion exchange, affinity, phosphocellulose, hydrophobic-interaction or hydroxylapatite chromatography, etc.). Desirably, the immune checkpoint modulator recombinantly produced for the oncolytic virus of the invention is at least partially purified in the sense that it is substantially free of other antibodies having different antigenic specificities and/or other cellular material. Further, the immune checkpoint modulator may be formulated according to the conditions conventionally used in the art (e.g. WO2009/073569).

Therapeutic Use

The present invention also provides a composition comprising a therapeutically effective amount of the oncolytic virus of the invention, optionally with a pharmaceutically acceptable vehicle. Such a compositions may be administered once or several times and via the same or different routes A "therapeutically effective amount" corresponds to the amount of oncolytic virus that is sufficient for producing one or more beneficial results. Such a therapeutically effective amount may vary as a function of various parameters, in particular the mode of administration; the disease state; the age and weight of the subject; the ability of the subject to respond to the treatment; kind of concurrent treatment; the frequency of treatment; and/or the need for prevention or therapy. When prophylactic use is concerned, the oncolytic virus or the composition of the invention is administered at a dose sufficient to prevent or to delay the onset and/or establishment and/or relapse of a pathologic condition (e.g. a proliferative disease such as cancer), especially in a subject at risk. For "therapeutic" use, the oncolytic virus or the composition of the present invention is administered to a subject diagnosed as having a pathological condition (e.g. a proliferative disease such as cancer) with the goal of treating the disease, eventually in association with one or more conventional therapeutic modalities. In particular, a therapeutically effective amount could be that amount necessary to cause an observable improvement of the clinical status over the baseline status or over the expected status if not treated, e.g. reduction in the tumor number; reduction in the tumor size, reduction in the number or extend of metastasis, increase in the length of remission, stabilization (i.e. not worsening) of the state of disease, delay or slowing of disease progression or severity, amelioration or palliation of the disease state, prolonged survival, better response to the standard treatment, improvement of quality of life, reduced mortality, etc. A therapeutically effective amount could also be the amount necessary to cause the development of an effective non-specific (innate) and/or specific anti-tumor immune response. Typically, development of an immune response in particular T cell response can be evaluated in vitro, in suitable animal models or using biological samples collected from the subject. For example, techniques routinely used in laboratories (e.g. flow cytometry, histology) may be used to perform tumor surveillance. One may also use various available antibodies so as to identify different immune cell populations involved in anti-tumor response that are present in the treated subjects, such as cytotoxic T cells, activated cytotoxic T cells, natural killer cells and activated natural killer cells. An improvement of the clinical status can be easily assessed by any relevant clinical measurement typically used by physicians or other skilled healthcare staff.

The term "pharmaceutically acceptable vehicle" is intended to include any and all carriers, solvents, diluents, excipients, adjuvants, dispersion media, coatings, antibacterial and antifungal agents, absorption agents and the like compatible with administration in mammals and in particular human subjects.

The oncolytic virus or the composition thereof can be placed in a solvent or diluent appropriate for human or animal use. The solvent or diluent is preferably isotonic, hypotonic or weakly hypertonic and has a relatively low ionic strength. Representative examples include sterile water, physiological saline (e.g. sodium chloride), Ringer's solution, glucose, trehalose or saccharose solutions, Hank's solution, and other aqueous physiologically balanced salt solutions (see for example the most current edition of Remington: The Science and Practice of Pharmacy, A. Gennaro, Lippincott, Williams&Wilkins).

In one embodiment, the oncolytic virus composition is suitably buffered for human use. Suitable buffers include without limitation phosphate buffer (e.g. PBS), bicarbonate buffer and/or Tris buffer capable of maintaining a physiological or slightly basic pH (e.g. from approximately pH 7 to approximately pH 9).

The oncolytic virus compositions may also contain other pharmaceutically acceptable excipients for providing desirable pharmaceutical or pharmacodynamic properties, including for example osmolarity, viscosity, clarity, colour, sterility, stability, rate of dissolution of the formulation, modifying or maintaining release or absorption into an the human or animal subject, promoting transport across the blood barrier or penetration in a particular organ.

The oncolytic virus compositions can also comprise one or more adjuvant(s) capable of stimulating immunity (especially a T cell-mediated immunity) or facilitating infection of tumor cells upon administration, e.g. through toll-like receptors (TLR) such as TLR-7, TLR-8 and TLR-9, including without limitation alum, mineral oil emulsion such as, Freunds complete and incomplete (IFA), lipopolysaccharide or a derivative thereof (Ribi et al., 1986, Immunology and Immunopharmacology of Bacterial Endotoxins, Plenum Publ. Corp., NY, p407-419), saponins such as QS21 (Sumino et al., 1998, J.Virol. 72: 4931; WO98/56415), imidazo-quinoline compounds such as Imiquimod (Suader, 2000, J. Am Acad Dermatol. 43:S6), S-27609 (Smorlesi, 2005, Gene Ther. 12: 1324) and related compounds such as those described in WO2007/147529, cytosine phosphate guanosine oligodeoxynucleotides such as CpG (Chu et al., 1997, J. Exp. Med. 186: 1623; Tritel et al., 2003, J. Immunol. 171: 2358) and cationic peptides such as IC-31 (Kritsch et al., 2005, J. Chromatogr Anal. Technol. Biomed. Life Sci. 822: 263-70).

In one embodiment, the oncolytic virus composition of the present invention may be formulated with the goal of improving its stability in particular under the conditions of manufacture and long-term storage (i.e. for at least 6 months, with a preference for at least two years) at freezing (e.g. −70° C., −20° C.), refrigerated (e.g. 4° C.) or ambient temperatures. Various virus formulation are available in the art either in frozen, liquid form or lyophilized form (e.g. WO98/02522, WO01/66137, WO03/053463, WO2007/056847 and WO2008/114021, etc.). Solid (e.g. dry powdered or lyophilized) compositions can be obtained by a process involving vacuum drying and freeze-drying (see e.g. WO2014/053571). For illustrative purposes, buffered formulations including NaCl and sugar are particularly adapted to the preservation of viruses (e.g. Tris 10 mM pH 8 with saccharose 5% (W/V), sodium glutamate 10 mM, and NaCl 50 mM or phosphate-buffered saline with glycerol (10%) and NaCl).

In certain embodiments, the oncolytic virus composition can be formulated to ensure proper distribution or a delayed release in vivo. For example, it can be formulated in liposomes. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g. J. R. Robinson in "Sustained and Controlled Release Drug Delivery Systems", ed., Marcel Dekker, Inc., New York, 1978.

The appropriate dosage of oncolytic virus can be adapted as a function of various parameters and may be routinely determined by a practitioner in the light of the relevant circumstances. Suitable dosage for the oncolytic virus varies from approximately $10^5$ to approximately $10^{13}$ vp (viral particles), iu (infectious unit) or pfu (plaque-forming units) depending on the virus and the quantitative technique used. As a general guidance, vaccinia virus doses from approximately $10^5$ to approximately $10^{13}$ pfu are suitable, preferably from approximately $10^6$ pfu to approximately $10^{11}$ pfu, more preferably from approximately $10^7$ pfu to approximately $5 \times 10^9$ pfu; doses of approximately $10^8$ pfu to approximately $10^9$ pfu being particularly preferred especially for human use. The quantity of virus present in a sample can be determined by routine titration techniques, e.g. by counting the number of plaques following infection of permissive cells using permissive cells (e.g. BHK-21 or CEF), immunostaining (e.g. using anti-virus antibodies; Caroll et al., 1997, Virology 238: 198-211), by measuring the A260 absorbance (vp titers), or still by quantitative immunofluorescence (iu titers).

In a preferred embodiment, the administration(s) of said oncolytic virus composition permits to deliver at least 50 ng/ml in a body sample obtained from the subject. In one embodiment, said level of immune checkpoint is obtained after a single administration of approximately $10^7$ pfu to approximately $5 \times 10^9$ pfu of the oncolytic virus described herein and can be further increased with subsequent administration(s). In another embodiment, the body sample is blood, serum, plasma, tumor biopsy, tumor homogenate, tumor fluid, etc. and is collected at least one hour to one month after said administration(s). More preferably, in situ production of the encoded immune checkpoint modulator reached at least 100 ng (e.g., at least 200ng/ml, at least 400 ng/ml, at least 500 ng/ml, at least 700 ng/ml, at least 800 ng/ml, at least 900 ng/ml, at least 1000 ng/ml, at least 1200 ng/ml, at least 1500 ng/ml, at least 1800 ng/ml, at least 2000 ng/ml, at least at least 2500 ng/m1 and at least 3000 ng/m1) per ml of said biological sample collected from the subject 2 to 8 days (e.g. 3 to 7 days or more preferably about 5 days) following the administration of said oncolytic virus. The levels of immune checkpoint inhibitor secreted in situ can be evaluated as described in the Examples.

Administration

The oncolytic virus or the composition of the present invention may be administered in a single dose (e.g. bolus injection) or multiple doses. If multiple administrations, they may be performed by the same or different routes and may take place at the same site or at alternative sites. It is also possible to proceed via sequential cycles of administrations that are repeated after a rest period. Intervals between each administration can be from several hours to one year (e.g. 24 h, 48 h, 72 h, weekly, every two weeks, monthly or yearly). Intervals can also be irregular (e.g. following tumor progression). The doses can vary for each administration within the range described above.

Any of the conventional administration routes are applicable in the context of the invention including parenteral, topical or mucosal routes. Parenteral routes are intended for administration as an injection or infusion. Common parenteral injection types are intravenous (into a vein), intra-arterial (into an artery), intradermal (into the dermis), subcutaneous (under the skin), intramuscular (into muscle) and intratumoral (into tumor or at its close proximity). Infusions typically are given by intravenous route. Mucosal administrations include without limitation oral/alimentary, intranasal, intratracheal, intrapulmonary, intravaginal or intra-rectal route. Topical administration can also be performed using transdermal means (e.g. patch and the like). Administrations may use conventional syringes and needles (e.g. Quadrafuse injection needles) or any compound or device available in the art capable of facilitating or improving delivery of the active agent(s) in the subject. Preferred routes of administration for the oncolytic virus include intravenous and intratumoral routes.

In the context of the invention, the oncolytic virus may be administered once or several time (e.g. 2, 3, 4, 5, 6, 7 or 8 times etc.) at a dose within the range of from $10^7$ to $5 \times 10^9$ pfu. The time interval between each administration can vary from approximately 1 day to approximately 8 weeks, advantageously from approximately 2 days to approximately 6 weeks, preferably from approximately 3 days to approximately 4 weeks and even more preferably from approximately 1 week to approximately 3 weeks (e.g. every two weeks for example). A preferred therapeutic scheme involves from 2 to 5 (e.g. 3) intravenous or intratumoral administrations of $10^8$ or $10^9$ pfu of oncolytic vaccinia virus at approximately 1 or 2 weeks interval.

The present invention also relates to a method for treating a proliferative disease such as cancer comprising administering an oncolytic virus as described herein to a subject in need thereof.

The present invention also relates to a method for inhibiting tumor cell growth in vivo comprising administering an oncolytic virus as described herein to a subject in need thereof.

The present invention also relates to a method for enhancing an immune response to tumor cells comprising administering an oncolytic virus as described herein to a subject in need thereof.

In one embodiment, the administration of the oncolytic virus for use in the present invention elicits, stimulates and/or re-orients an immune response. In particular, the administration induces a protective T or B cell response in the treated host, e.g. against said oncolytic virus or eventually against the product encoded by the therapeutic gene(s) inserted in the viral genome if any. The protective T response can be CD4+ or CD8+ or both CD4+and CD8+cell mediated. B cell response can be measured by ELISA and T cell response can be evaluated by conventional ELISpot, ICS assays from any sample (e.g. blood, organs, tumors, etc.) collected from the immunized animal or subject.

In one embodiment, the administration of the oncolytic virus permits to change tumor microenvironment with the goal of enhancing activity of effector cells in the tumor, especially effector T lymphocytes and/or promoting at least partial Treg depletion. Tumor infiltrating cells can be easily identified for examples by conventional immunostaining assays.

In one embodiment the method of the invention provides a higher therapeutic efficacy than the one obtained in the same conditions with a similar oncolytic virus (without immune checkpoint modulator) or the immune checkpoint modulator either individually or even in co-administration. In the context of the invention, the method of the invention provides at least 5%, at least 10%, at least 15%, at least 20%, or at least 25% more therapeutic efficacy than either the virus or the immune check point modulator alone or in co-administration. A higher therapeutic efficacy could be evidenced as described above in connection with the term "therapeutically effective amount" with a specific preference for a longer survival.

Examples of proliferative diseases that may be treated using the oncolytic virus, composition or methods of the invention include bone cancer, liver cancer, pancreatic cancer, stomach cancer, colon cancer, cancer of the esophagus, oralpharyngeal cancer, lung cancer, cancer of the head or neck, skin cancer, melanoma, uterine cancer, cervix cancer, ovarian cancer, breast cancer, rectal cancer, cancer of the anal region, prostate cancer, lymphoma, cancer of the endocrine system, cancer of the thyroid gland, sarcoma of soft tissue, chronic or acute leukemias, cancer of the bladder, renal cancer, neoplasm of the central nervous system (CNS), glioma, etc. The present invention is also useful for treatment of metastatic cancers, especially metastatic cancers that express PD-L1 (Iwai et al., 2005, Int. Immunol. 17: 133-44). Preferred cancers that may be treated using the oncolytic virus of the invention include cancers typically responsive to immunotherapy. Non-limiting examples of preferred cancers for treatment include melanoma (e.g. metastatic malignant melanoma), renal cancer (e.g. clear cell carcinoma), prostate cancer (e.g. hormone refractory prostate adenocarcinoma), breast cancer, colorectal cancer, lung cancer (e.g. non-small cell lung cancer) and liver cancer (e.g. hepatocarcinoma).

According to an advantageous embodiment, especially when the oncolytic virus is armed with a suicide gene, the oncolytic virus therapy or methods according to the present invention may comprise an additional step in which pharmaceutically acceptable quantities of a prodrug, advantageously an analog of cytosine, in particular 5-FC, are administered to the subject. By way of illustration, it is possible to use a dose of from 50 to 500 mg/kg/day, with a dose of 200 mg/kg/day or of 100 mg/kg/day being preferred. Within the context of the present invention, the prodrug is administered in accordance with standard practice (e.g. per os, systematically, etc.). Preferably, the administration taking place subsequent to the administration of the oncolytic virus, preferably at least 3 days, more preferably at least 4 days and even more preferably at least 7 days after the administration of the virus. The oral route is preferred. It is possible to administer a single dose of prodrug or doses which are repeated for a time which is sufficiently long to enable the toxic metabolite to be produced within the host organism or cell.

The oncolytic virus, composition or method according to the invention can be associated with one or more substances or therapy effective in anticancer therapy and the present invention also concerns a method which comprises the step of delivering to the subject an additional cancer therapy. In the context of the present invention, said additional cancer therapy comprises surgery, radiation, chemotherapy, immunotherapy, hormone therapy or a combination thereof. In a preferred embodiment the method of the invention comprises the administration of one or more substances effective in anticancer therapy. Among pharmaceutical substances effective in anticancer therapy which may be used in association or in combination with the oncolytic virus, composition or method according to the invention, there may be mentioned more specifically:
  alkylating agents such as e.g. mitomycin C, cyclophosphamide, busulfan, ifosfamide, isosfamide, melphalan, hexamethylmelamine, thiotepa, chlorambucil, or dacarbazine;
  antimetabolites such as, e.g. gemcitabine, capecitabine, 5-fluorouracil, cytarabine, 2-fluorodeoxy cytidine, methotrexate, idatrexate, tomudex or trimetrexate;
  topoisomerase II inhibitors such as, e.g. doxorubicin, epirubicin, etoposide, teniposide or mitoxantrone;
  topoisomerase I inhibitors such as, e.g. irinotecan (CPT-11), 7-ethyl-10-hydroxy-camptothecin (SN-38) or topotecan;
  antimitotic drugs such as, e.g., paclitaxel, docetaxel, vinblastine, vincristine or vinorelbine;
  platinum derivatives such as, e.g., cisplatin, oxaliplatin, spiroplatinum or carboplatinum;
  inhibitors of tyrosine kinase receptors such as sunitinib (Pfizer) and sorafenib (Bayer);
  anti-neoplastic antibodies in particular antibodies that affect the regulation of cell surface receptors such as trastuzumab, cetuximab, panitumumab, zalutumumab, nimotuzumab, matuzumab, bevacizumab and ranibizumab;
  EGFR (for Epidermal Growth Factor Receptor) inhibitors such as gefitinib, erlotinib and lapatinib; and
  immunomodulatory agents such as, e.g. alpha, beta or gamma interferon, interleukin (in particular IL-2, IL-6, IL-10 or IL-12) or tumor necrosis factor;

The oncolytic virus, composition or method according to the invention can also be used in association with radiotherapy.

The present invention also provides kits including a different container (e.g., a sterile glass or plastic vial) for each virus dose to be administered. Optionally, the kit can include a device for performing the administration of the active agents. The kit can also include a package insert including information concerning the compositions or individual component and dosage forms in the kit.

BRIEF DESCRIPTION OF THE DRAWINGS

FIG. 4 illustrates the amino acid sequences of the heavy and light chains of the anti-PD1 antibodies expressed by the oncolytic vaccinia virus described herein.

EXAMPLES

Figure 1:
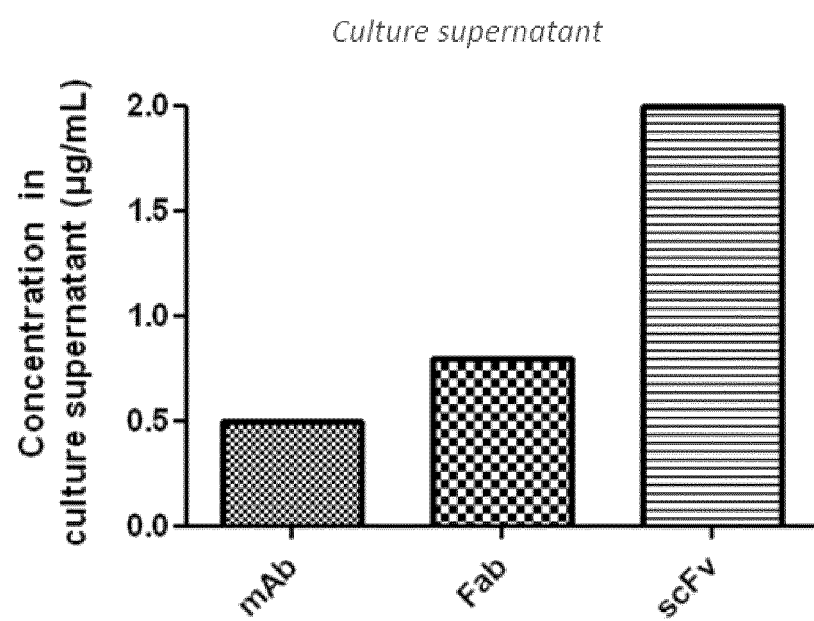
FIG. 1 illustrates the quantity of purified anti-PD-1 mAb, Fab and scFv produced from infected CEF.

These examples illustrates oncolytic vaccinia virus engineered for expressing various forms of anti-immune checkpoint inhibitors. Preclinical evidence for the beneficial effects of expressing immune checkpoint blockers from viral vectors was to be demonstrated in mouse tumor models. This implies the use of i) murine-specific anti-immune check point antibodies and ii) an oncolytic poxvirus capable of infecting murine cells with a higher efficacy.

The murine-specific hamster antibody J43 was chosen to target the immune checkpoint blocker murine PD-1 (mPD-1). This antibody was shown to block the interaction of mPD1 with PD-L1 (U.S. Pat. No. 7,858,746). The antibody J43 and its isotype control (hamster IgG) are available from BioXCell. The anti mPD-1 antibodies and its isotype control were used to establish functional tests and quantitative ELISA in vitro. Further, J43 and various forms thereof were cloned in an oncolytic virus and tested in vivo in tumor animal models.

The oncolytic virus chosen for these studies is a vaccinia virus (VV) Western Reserve (WR) strain defective for thymidine kinase (TK) (locus J2R) and RR⁻ (locus I4L) rendering the virus non-replicative in healthy (non-dividing) cells. In contrast, the VV TK⁻RR⁻ is supposed to selectively and efficiently replicate in tumor cells.

Vectorization of anti mPD-1 Molecules in Oncolytic TK⁻RR⁻ vaccinia virus.

The heavy chain of J43 showed high homology with the heavy chain of anti CD79b IgG. Thus, the sequence retained for cloning of the heavy chain was the variable chain of J43 and the constant chain of anti CD79b. The light chain of J43 was cloned with signal sequence from the light chain of anti CD79b antibody. The heavy and light chains were put under the control of the viral promoters pH5R or p7.5K which have slightly different strengths. Further to "whole" antibody constructs, derivatives were generated, respectively His-tagged antigen binding fragments (Fab) constructs as well as a His-tagged single chain antibody (scFv) constructs. Two construct formats were also generated for Fab depending on the light or heavy chain portions placed under each promoter. All five constructs were inserted in the backbone of TK, RR deleted WR VV. The constructs are summarized below:

WRTG18618 (or mAb1) corresponding to pH5R-HC-p7.5K-LC

WRTG18619 (or mAb2) corresponding to pH5R-LC-p7.5K-HC

WRTG18621 (or Fab1) corresponding to pH5R-(VH-CH1-6His)-p7.5K-LC

WRTG18620 (or Fab2) corresponding to pH5R-LC-p7.5K-(VH-CH1-6His)

WRTG18616 (scFv) corresponding to pH5R-VH-gs-VL-6His).

HC and LC represents the abbreviation of heavy and light chains, VH and VL of heavy and light variable domains, 6His of the HIS tag (6 histidines) and gs (poly Glycine-Serine linker)

Constructs 1 demonstrated the highest expression level of the recombinant mAb or Fab with the expected chain assembly profiles.

Virus stocks WRTG18616 (scFv), WRTG18618 (mAb1) and WRTG18621 (Fab1) were produced in BHK-21 cells and purified by tangential flow filtration (TFF).

Construction of WRTG18618 (pH5R-HC-p7.5K-LC): mAb1

Fragment containing HC followed by p7.5K promoter was generated by synthetic way (Geneart: Regensburg, Germany) and was cloned in vaccinia transfer plasmid pTG18496 restricted by PstI and EcoRI to give pTG18614. Fragment containing LC was generated by synthetic way and was cloned in pTG18614 restricted by NsiI and SalI to give pTG18618.

The vaccinia transfer plasmid, pTG18496, is designed to permit insertion of the nucleotide sequence to be transferred by homologous recombination in TK gene of the VV genome. It contains the flanking sequences (BRGTK and BRDTK) surrounding the J2R gene and the pH5R promoter followed by multiple cloning sites.

The amino acid sequences of the anti-PD-1 HC and LC are given in SEQ ID NO: 1 and SEQ ID NO: 2, respectively and in FIG. 4.

Generation of WRTG18618 was performed by homologous recombination in primary chicken embryos fibroblasts (CEF) infected with a RR-deleted WR and transfected by nucleofection with pTG18618 (according to Amaxa Nucleofector technology). Viral selection was performed by plaque purification after growth in Thymidine kinase-deficient (TK⁻) 143B cells cultured in the presence of bromodeoxyuridine. This selection allows only TK⁻ rWR to remain viable. Absence of contamination by parental WR was verified by PCR.

Construction of WRTG18619 (pH5R-LC-p7.5K-HC): mAb2

Fragment containing LC followed by p7.5K promoter was generated by synthetic way and was cloned in vaccinia transfer plasmid pTG18496 restricted by PstI and EcoRI to give pTG18615. Fragment containing HC was generated by synthetic way and was cloned in pTG18615 restricted by NsiI and MluI to give pTG18619.

Generation of WRTG18619 virus was performed in CEF by homologous recombination as described above.

Construction of WRTG18621 (pH5R-(VH-CH1-6His)-p7.5K-LC): Fab1

Fragment containing VH-CH1-6His followed by p7.5K promoter was generated by synthetic way and was cloned in vaccinia transfer plasmid pTG18496 restricted by PstI and EcoRI to give pTG18617. Fragment containing LC was generated by synthetic way and was cloned in pTG18617 restricted by NsiI and SalI to give pTG18621.

Generation of WRTG18621 virus was performed in CEF by homologous recombination as described above.

Construction of WRTG18620 (pH5R-LC-p7.5K-(VH-CH1-6His): Fab2

Fragment containing LC followed by p7.5K promoter was generated by synthetic way and was cloned in vaccinia transfer plasmid pTG18496 restricted by PstI and EcoRI to give pTG18615. Fragment containing VH-CH1-6His was generated by synthetic way and was cloned in pTG18615 restricted by NsiI and MluI to give pTG18620.

Generation of WRTG18620 virus was performed in CEF by homologous recombination as described above.

Construction of WRTG18616 (pH5R-VH-gs-VL-6His): scFv

Fragment containing VH-gs-VL-6His was generated by synthetic way and was cloned in vaccinia transfer plasmid pTG18496 restricted by PstI and EcoRI to give pTG18616.

Generation of WRTG18616 virus was performed in CEF by homologous recombination as described above.

In vitro characterization of the encoded anti-PD-1 antibodies

The recombinant oncolytic vectors described above were tested to assess the production of the encoded anti-mPD-1 molecules. To this, permissive primary cells or cell lines were infected, and supernatant harvested. Presence of anti-mPD-1 molecules can be determined by SDS-PAGE, Western blot analysis, mass spectrometry analysis, ELISA and functional assays. Commercially available anti-mPD-1 antibodies were used as controls.

Supernatant from infected CEF (moi 0.2) were analyzed (after 48 and 72 h post infection) by Western Blot under non-reducing conditions using a polyclonal anti-hamster IgG antibody for detection. WRTG18618 (mAb1) and WRTG18621 (Fab1) could be detected by ELISA. Expression profile of the product secreted by WRTG18618-infected cells has similar pattern as commercial J43 antibody and expected assembly of the product secreted by WRTG18621-infected cells was observed. ScFv expression was also detected in culture supernatant by Western Blot at the expected size.

mAb Purification and in vitro Assessment of Anti PD-1 Antibodies

CEF were cultured in F175 flasks and infected with $2.7 \times 10^8$ pfu of anti-PD-1-expressing viruses. After 48-72 h, culture supernatants were collected and subjected to filtration on 0.2 µm filters. mAb1 was purified by Hitrap protein A (GE Healthcare) followed by Superdex 200 gel filtration (GE Healthcare) whereas Fab1 and scFv were purified by HIS-Trap (GE Healthcare) followed by Superdex 75 gel filtration (GE Healthcare). scFv eluted from gel filtration in two peaks, the first one corresponding to dimers and the second one to monomers. Significant amounts of mAbs, Fab and scFv were produced as shown in FIG. 1. The yield is between 0.5 and 2 µg/ml supernatant according to the antibody format.

Figure 2:
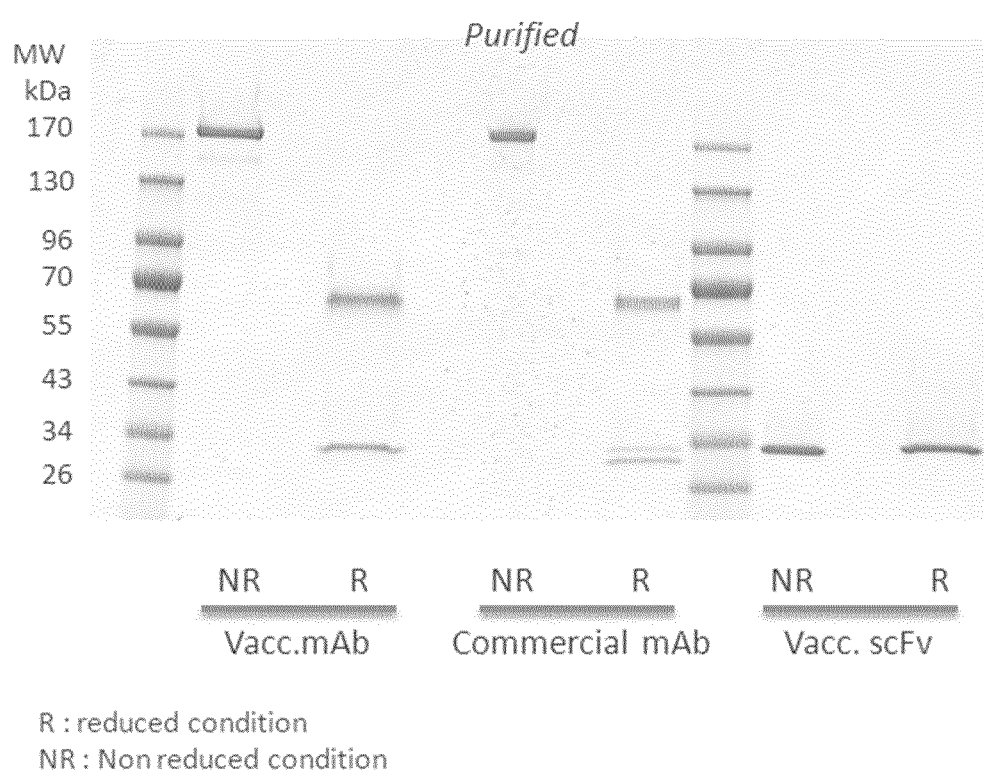
FIG. 2 illustrates an analysis by electrophoresis of the purified recombinant mAb (Vacc.mAb) and scFv (Vacc.scFv) as well as commercial J43 (BioXCell) under reduced (R) and non reduced (NR) conditions.

Recombinant purified mAb had an electrophoresis profile similar to the commercial mAbs with the correct assembly of the two light and two heavy chains under non reducing conditions and the detection of the individual light and heavy chains under reducing conditions as illustrated in FIG. 2. Moreover, purified scFv migrated on SDS-PAGE at the expected size (see FIG. 2).

The recombinant products can be detected by ELISA and are functional in a competition ELISA (i.e. blocking of binding of mouse PD-L1 biot at 0.2 µg/mL to mouse PD-1 coated at 1 µg/mL), mAb being more efficient than Fab in this competition experiment. Moreover, the recombinant mAb1 is more efficient than its commercial J43 counterpart as well as VV-produced scFv dimeric fraction is more efficient than the monomeric one with a difference of approximately one log in EC50.

The ability of VV-encoded mAb1, Fab1 and scFv to interact with cell-surface PD-1 was studied in flow cytometry-based binding assays using the PD-1-positive T lymphoma cell lines EL4 and RMA. $10^5$ EL4 or RMA cells were incubated for 45 min on ice with 100 µl of either mAb1 (5 µg/ml), commercially available anti-mPD-1 antibody J43 (5 µg/ml, BioXCell) or negative control hamster IgG (5 µg/ml, BioXCell) and washed. Binding to PD-1 was detected by incubating cells for 45 min on ice with 100 µl of 10 µg/ml FITC-conjugated monoclonal mouse anti-Armenian+Syrian antibody cocktail (BD Pharmingen). After washing, fluorescence intensity was measured on a Navios™ flow cytometer (Beckman Coulter). Data were analysed using Kaluza 1.2 software (Beckman Coulter). WRTG18618-encoded mAb1 bound efficiently to EL4 and RMA cells.

To measure the binding of Fab1 and scFv, $5 \times 10^5$ EL4 or RMA cells were indirectly stained with either 5 µg/ml Fab1 or 2.5 µg/ml monomeric scFv (which are both His-tagged) followed by PE-conjugated monoclonal mouse anti-His tag antibody (diluted 1/10, Miltenyi Biotec) and analysed as described above. Fab1 and monomeric scFv produced from WRTG18621 and WRTG18616 were shown to bind efficiently to the surface of EL4 and RMA cells. Specific binding could be demonstrated by co-incubating EL4 cells with Fab1 or monomeric scFv and full-length J43 or negative control hamster IgG from BioXCell, followed by staining with PE-conjugated anti-His tag antibody. EL4 staining was reduced in the presence of full-length J43 but not negative control hamster IgG. Altogether, the results demonstrated that VV-encoded mAb1, Fab1 and scFv were able to recognize endogenously expressed PD-1 in two murine T lymphocyte cell lines.

A flow cytometry-based competition assay was established to compare blocking activity of anti-mPD-1 molecules. The assay is based on the murine T lymphoma cell line EL4 which is highly PD-1 positive. The binding of mPD-L1-hFc (murine PD-Ligand 1 comprising human IgG Fc fragment) to the cell-surface PD1 can be detected by flow cytometry using a PE-labeled anti-hFc monoclonal antibody. Binding of mPD-L1-hFc can be competed for by anti-PD-1 antibodies leading to reduction of cell-bound PE signal.

The inhibitory activity of recombinant mAb1, Fab1 and scFv on PD-L1 binding to EL4 cells was assessed and compared to commercially available J43 anti-PD-1 antibody (BioXCell). More specifically, $10^5$ EL4 cells were co-incubated with 2 µg/ml of mPD-L1 hFc (R&D Systems) and increasing concentrations of the various anti-PD-1 antibodies in 100 µl for 45 min on ice. After washing, cells were incubated with 100 µl of 5 µg/ml PE-conjugated mouse anti-human IgG Fc (BioLegend) for 45 min on ice. Cells were washed and the mean fluorescence intensity was measured as described above. In these conditions, the control anti mPD-1 clone J43 showed an $IC_{50}$ of 1.6 µg/ml.

As expected, the control hamster IgG did not show any blocking activity on PD-L1 binding to EL4 cells. The recombinant mAb1, Fab1, monomeric and dimeric scFv produced respectively from WRTG18618, WRTG18621 and WRTG18616 were able to block ligand binding to cell-surface receptor as J43 from BioXCell. Importantly, WRTG18618-encoded mAb1 exhibited enhanced blocking activity as compared to J43 from BioXCell and Fab1 and scFv versions in this assay.

A quantitative ELISA was established to quantify antibody concentrations produced in mouse serum or by recombinant WR-infected cells using coated rabbit-derived anti hamster antibodies to capture J43, which could be detected in return with a goat-derived anti hamster antibody. The assay is sensitive to mouse serum and standard curves have to be generated in the presence of 50% mouse serum.

In vitro cytotoxicity assay (oncolytic activity)

Figure 3:
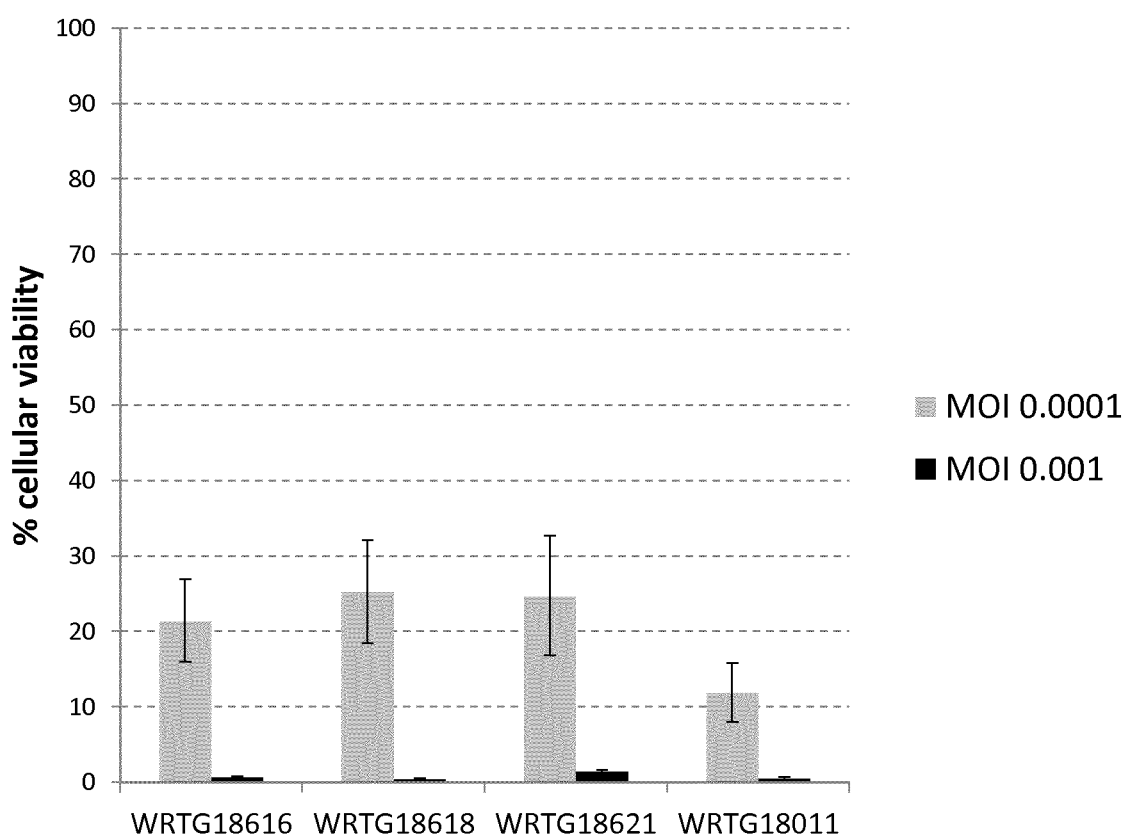
FIG. 3: In vitro replication efficacy of viruses in LoVo infected at a MOI of 0.0001, 0.001 and 0.01 with the indicated viruses at day 5 post infection. Values are represented in mean ±SD of three individual determinations.

Human LoVo colon cancer cell line was transduced in suspension at a MOI of 0.001 and 0.0001 by TK-RR deleted WR vaccinia virus without transgene (WRTG18011) and by TK-RR-deleted WR vaccinia virus expressing the different anti mPD-1 molecules (WRTG18616, WRTG18618 and WRTG8621). A total of $3 \times 10^5$ cells/well were plated in 6-well culture dishes in 2 ml of medium supplemented with 10% FCS. Cells were then cultured at 37° C. and cell survival was determined 5 days later by trypan blue exclusion. As shown in FIG. 3, the oncolytic activity of the different viruses resulted in 75-95% and 99% reduction in viable cell number at a MOI of 0.0001 and 0.001, respectively. TK-RR-deleted WR virus without transgene and TK-RR deleted WR virus expressing the different anti mPD-1 molecules showed no difference in cytotoxicity. Thus the expression of the different anti mPD-1 molecules did not affect the oncolytic activity of the vaccinia virus.

Optimal Design for Antibody Expression

The recombinant oncolytic vectors were tested by Immunoblotting to assess expression levels and assembly of the secreted antibodies. Immunoblot analyses were performed on cell culture supernatants collected 24 h after CEF infection with mAb and Fab constructs described above. Supernatant were centrifuged 5 min at 16000 g and 25 µl were prepared in Laemmli buffer without reducing agent and loaded on PrecastGel 4-15% polyacrylamide gel (Biorad). Monoclonal commercial J43 (BioXcell) was used as reference molecule. One µg of each molecule was loaded on gel. Gel electrophoresis was performed in non-reducing conditions to preserve the assembly of light and heavy chains and allow an optimal detection (i.e. the polyclonal antibody used for detection did not recognized reduced IgG and Fab chains). Proteins were then transferred onto a PVDF membrane using the Trans-blot Turbo system (Transblot Turbo Transfer pack Biorad) with the preprogrammed protocol (High MW: 10 min; 2.5 A constant; up to 25V). Membranes were saturated overnight at 4° C. in blocking solution (8 mM $NaPO_4$, 2 mM $KPO_4$, 154 mM NaCl pH 7.2 (PBS) supplemented with 0.05% Tween20, 5% Nonfat dry milk Biorad). Horseradish peroxidase (HRP) conjugated goat anti Armenian Hamster IgG (Jackson Immunoresearch) at 80 ng/mL in dilution buffer (PBS, 0.05% Tween20, 0.5% Nonfat dry milk) was used for the antibody immunodetection. Development was performed with Amersham ECL Prime Western Blotting detection reagents and Molecular Imager Chemi-DOC™ XRS was used to capture chemiluminescence.

Figure 5:
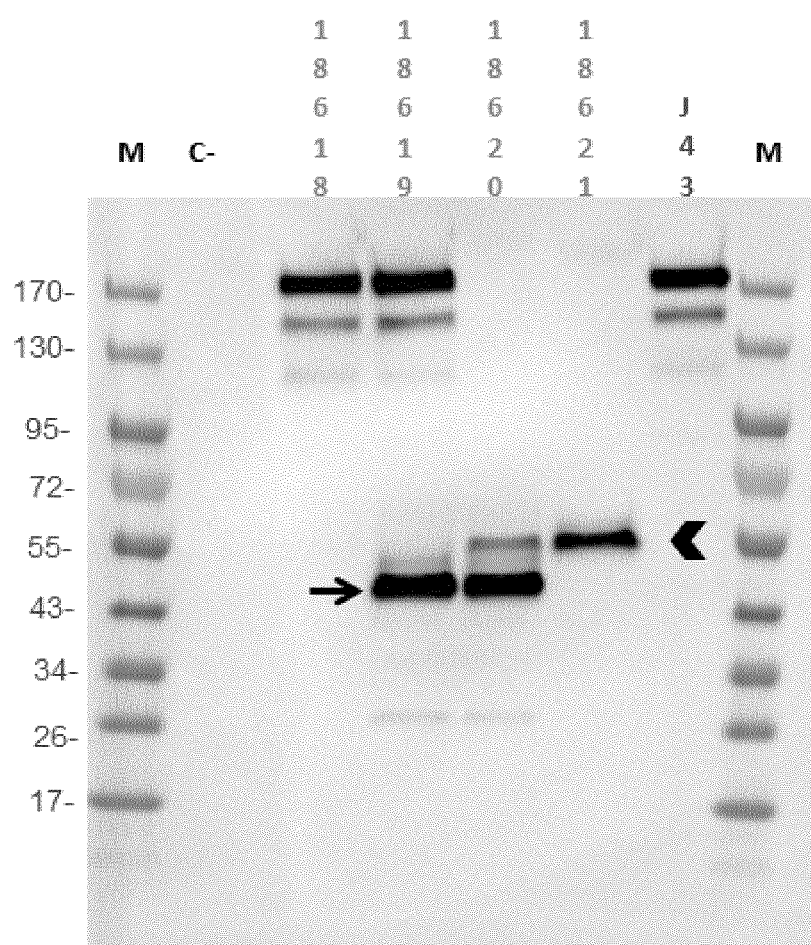
FIG. 5 illustrates immunoblot analysis of the recombinant mAb and Fab secreted in cell culture supernatants obtained from CEF infected with WRTG18618, WRTG18619, WRTG18620 and WRTG18621. Commercial J43 is used as reference; M represents MW markers and C negative control.

As illustrated in FIG. 5, both WRTG18618 and WRTG18619 secreted roughly the same quantities of an antibody product with an apparent size corresponding to two heavy and two light chains linked together comparable to that of commercial J43 mAb. However, WRTG18619 also produced a non-expected product migrating between 43 and 55 kDa markers (see the extra band indicated by an arrow in the fourth lane "18619"). Similarly, an extra band was also present in the WRTG18620-infected culture supernatant (same position and same intensity in the fifth lane "18620") whereas WRTG18621 produced high amount of correctly assembled Fab without any detectable misassembled product (see arrow head in the sixth lane "18621").

Analyses of cell culture supernatants generated after infection of mammal cell lines BHK21 and A549 generated the same profile (data not shown).

When looking at the construct design, it appears that in both WRTG18619 and WRTG18620 constructs, the antibody light chain was placed under the transcriptional control of pH5R promoter (a strong promoter). One hypothesis is that in this configuration, antibody light chains could be overexpressed with respect to heavy chains and thus can assemble in homodimers. Therefore, this extra band, migrating between 43 and 55 kDa, could correspond to overproduced light chains that have assembled into a homodimer of a theoretical mass of 47 kDa.

Therefore, it is preferable to express heavy chain under the control of a stronger promoter than the one used to express light chains in order to reduce the risk of generating aberrant assembly (e.g. homodimers of light chains)

All together these results confirmed the ability of the recombinant oncolytic viruses described herein to secrete mAb and Fab at detectable level. WRTG18618 and WRTG18621 were selected for the rest of experiments due to their capacity to produce antibody products that are closer to expectation than those of WRTG18619 and WRTG18620.

In vivo expression of vectorised anti-PD1 antibody

Expression of the vectorized anti-PD-1 J43mAb was evaluated in vivo in mice with and without subcutaneously-implanted B16F10 tumors. WRTG18618 (mAb1 construct) was injected either intra-tumorally or subcutaneously and compared to commercial J43 (intra-tumoral injection).

In vivo Experiments and Sample Collection

More specifically, $3 \times 10^5$ B16F10 cells (murine melanoma) were injected subcutaneously (S.C.) into the right flanks of six weeks old female C57BL/6 mice. At day 0 (D0), when tumor volumes reached 100-200 mm³, 100 microliters of either WRTG18618 ($10^7$ pfu) or commercial J43 (1 μg or 10 μg, Bioxcell) were injected intra-tumorally (I.T.).

WRTG18618 was also injected S.C. in mice without tumor.

Blood and tumors were collected at D1, D5 and D11. For each time point, 3 mice were anesthetized with 200 μL pentobarbital and the blood was collected by intra-cardiac puncture. The blood was stored at 4° C. during 8 hours and the serum was recovered after two centrifugations and kept at −20° C. until analysis. After blood sampling, mice were sacrificed by cervical elongation and the tumor recovered. Tumors were weighted, cut into small pieces and transferred in GentleMACS C-type tubes (Miltenyi) containing 3 ml PBS. Tumors were mechanically dissociated applying program "m-imptumor01" (GentleMacs, Miltenyi). After centrifugation at 300 g for 7 min, supernatants were recovered and kept at −20° C. until analysis.

J43 concentration was measured by quantitative ELISA both in serum and in tumor homogenates at different time points after virus or commercial J43 mAb injections.

Quantitative ELISA

J43 concentrations was evaluated both in serum and tumor homogenates. More specifically, ninety six wells plates (Nunc immune plate Maxisorp) were incubated overnight at 4° C. with 100 μL/well of 0.8 μg/mL of goat anti-hamster IgG (Southern Biotech) in coating solution (0.05 M Na carbonate pH 9.6, Sigma). Plates were washed three times with wash buffer (300 μL/well of PBS, 0.05% Tween20) and incubated 1 h at RT with 200 μL/well of blocking solution (PBS, 0.05% Tween 20, 5% Non Fat Dry Milk). Plates were washed three times with washing buffer. A standard range of J43 (BioXcell) was prepared in 100% mouse serum (Sigma) from 1000 to 0.488 ng/mL by 2 fold serial dilutions. Each standard was then further diluted 2 fold in blocking solution (final J43 concentration from 500 to 0.244 ng/mL) to have a final concentration of serum of 50%. One hundred μL/well of each standard were added in duplicate on the plate. Samples of serum were diluted at least two fold in blocking buffer, and if necessary further diluted in 1Vol/1Vol mix of blocking buffer/serum and 100 μL were added to the plates. The plates were incubated 2 h at 37° C. After 3 washes with wash buffer, 100 μL/well of HRP conjugated goat anti Armenian Hamster IgG (Jackson Immunoresearch) at 80 ng/mL were added and plates were incubated 1 h at 37° C. After 3 washes, 100 μL/well of 3,3',5,5'-tetramethylbenzidine (TMB, Sigma) were added and the plates incubated at RT for 30 min. The reaction was stopped with 100 μL/well of 2 M $H_2SO_4$ and the absorbance was measured at 450 nm with a plate reader (TECAN Infinite M200 PRO). The OD values obtained were transferred to the software GraphPadPrism and samples concentrations were back-calculated using the standard curve fitted with 5 parameters.

Figure 6A:
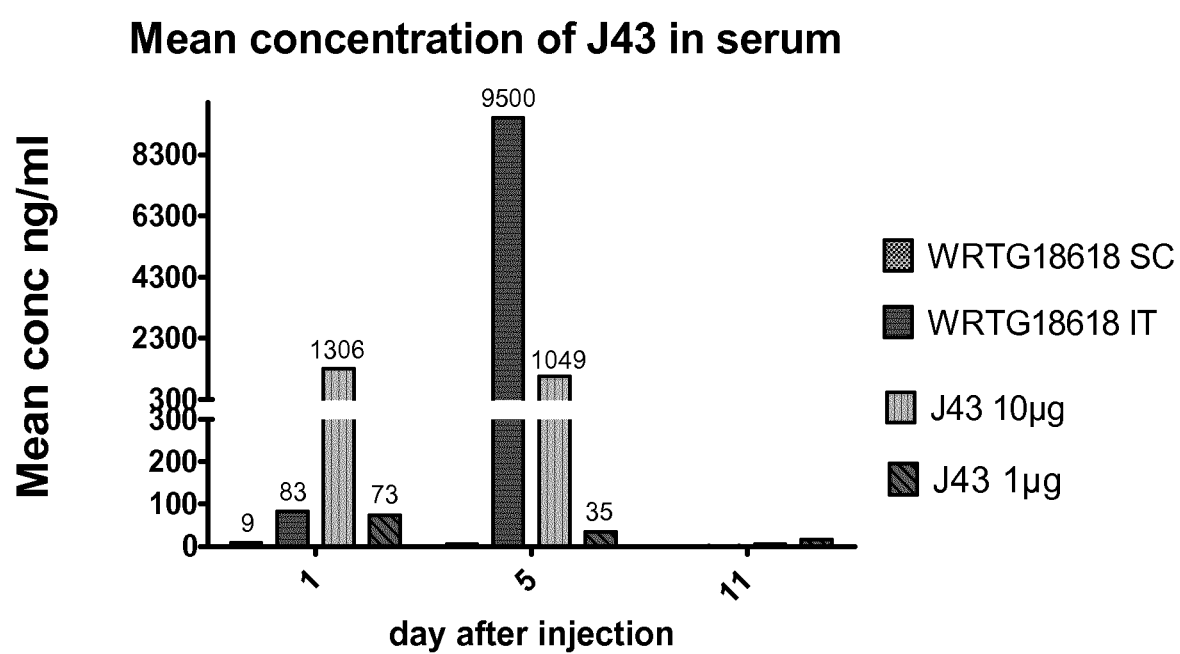
FIG. 6 illustrates the concentration of recombinant J43 produced in the serum (FIG. 6A) and in tumor homogenate (FIG. 6B) of mice treated with a single administration of WRTG18618 ($10^7$ pfu) injected intratumorally (resulting from subcutaneous implantation of B16F10 tumors) or subcutaneously (mice without tumors) or with intratumoral administration of 1 µg or 10 µg of commercial J43 (Bioxcell). Concentration of recombinant J43 was measured by quantitative ELISA 1, 5 and 11 days after injection.

As shown in FIG. 6A, when injected subcutaneously in a naive mice (no tumors implanted), production of recombinant J43 from WRTG18618 was very weak (9 ng/ml at day 1 and 4.5 ng/ml at day 5). In contrast, high quantities of recombinant J43 were secreted in serum of mice bearing B16F10 tumors following intratumoral WRTG18618 injection, respectively 9 and 1900 times higher at D1 and D5 (83 ng/ml and 9500 ng/ml) than the concentration of recombinant J43 measured after subcutaneous virus injection. This result suggests that the oncolytic virus is multiplying preferentially in tumors rather than in subcutaneous healthy tissues. In comparison, seric concentrations found after intratumoral injection of 10 μg commercial J43 reached around 1000 ng/ml (1306 ng/ml at D1 and 1049 ng/ml at D5) whereas the seric concentrations were much lower with 1 μg of commercial J43 (73 ng/ml at D1 and 35 ng/ml at D5).

Figure 6B:
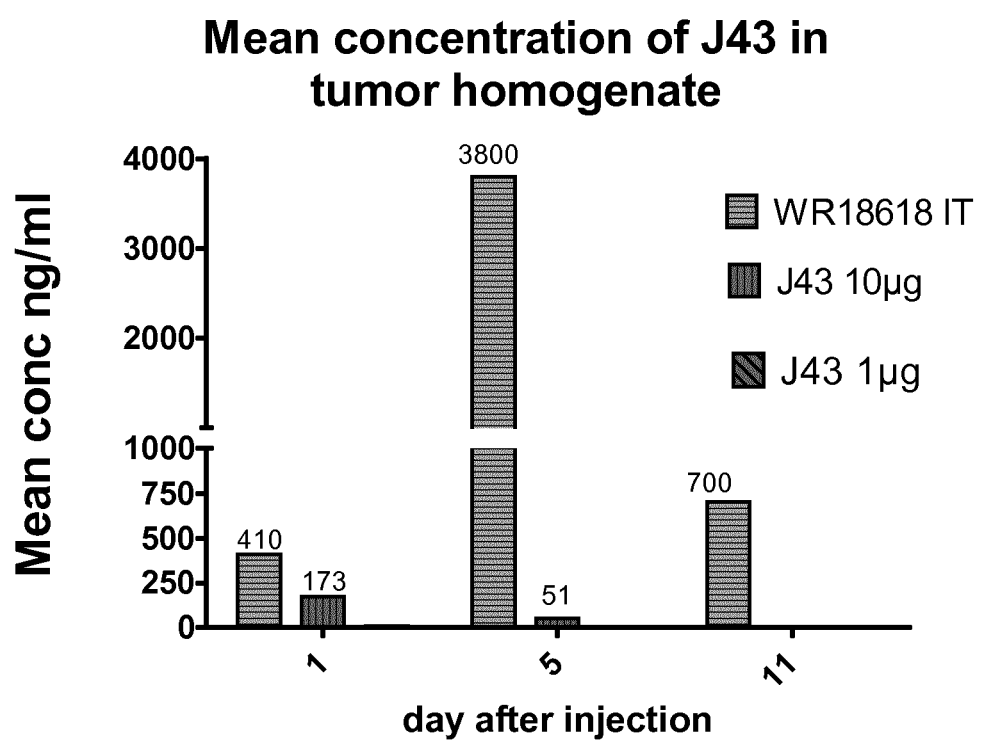

In tumor homogenates, the production of recombinant J43 followed the same trend as in serum with a peak of concentration at D5 (see FIG. 6B). The pharmacokinetics of J43 after a single IT injection of commercial mAb or WRTG18618 are very different. Following IT injection of 10 µg of commercial J43, the maximum antibody concentration was measured in serum and in tumor at D1 (1306 ng/ml and 173 ng/ml respectively) as expected, whereas IT injection of WRTG18618 resulted in maximum seric and tumor concentrations at D5 (9500 ng/ml and 3800 ng/ml, respectively). It should be highlighted that tumor concentrations of recombinant J43 produced after virus IT injection were much higher than those measured after IT injection of 10 µg commercial J43 at all time points (410 ng/ml versus 173 ng/ml at D1; 3800 ng/ml versus 51 ng/ml at D5 and 700 ng/ml versus under detection limit at D11). Importantly, antibody production was still detected in tumors at D11 after virus treatment, which is not the case after commercial J43 injection.

These data suggest that vectorization of J43 in oncolytic viruses allow a higher and longer accumulation of antibody in tumors compared to IT injection of commercial antibody.

Antitumor Activity in Subcutaneous Tumor Model

Antitumor activity of the various anti-PD-1-expressing vaccinia viruses described above may be tested in conventional preclinical models after implantation of tumors followed by injection of the constructs. For example, murine cancer cells are injected subcutaneously into the flanks of immunocompetent mice. When tumors reached a volume of 50-70 mm$^3$, the mice are randomized in a blinded manner and treated with the indicated vaccinia virus at a dose of $1\times10^7$ PFU. The vectors or control vehicle (buffer used to resuspend the virus) are directly injected into the tumor at days 10, 12 and 14 after tumor implantation. Tumor size is measured twice weekly using callipers. In particular, vectorised scFv and mAb1 antibody are at least as efficient as the co-administration of a WR vector with commercial J43 to delay tumor growth and increase survival rate.

Those skilled in the art will recognize, or be able to ascertain using no more than routine experimentation, numerous equivalents to the specific method and reagents described herein, including alternatives, variants, additions, deletions, modifications and substitutions. Such equivalents are considered to be within the scope of this invention and are covered by the following claims.

The invention claimed is:

1. An oncolytic virus comprising inserted in its genome a nucleic acid molecule encoding one or more immune checkpoint modulator(s), wherein said virus is a vaccinia virus defective for thymidine kinase (TK) resulting from inactivating mutations in the J2R viral gene and defective for Ribonucleotide reductase (RR) activity resulting from inactivating mutations in only the viral I4L gene, and wherein said one or more immune checkpoint modulator(s) is selected from antibodies that specifically bind to PD-L1, PD-L2, LAG3, Tim3, BTLA, or CTLA4.

2. The oncolytic virus of claim 1, wherein said vaccinia virus is selected from the group of Elstree, Wyeth, Copenhagen, and Western Reserve strains.

3. The oncolytic virus of claim 1, wherein said oncolytic virus further comprises at least one therapeutic gene inserted in the viral genome.

4. The oncolytic virus of claim 3, wherein said therapeutic gene is selected from the group consisting of genes encoding suicide gene products and genes encoding immunostimulatory proteins.

5. The oncolytic virus of claim 4, wherein said suicide gene is selected from the group consisting of genes coding protein having a cytosine deaminase (CDase) activity, a thymidine kinase activity, an uracil phosphoribosyl transferase (UPRTase) activity, a purine nucleoside phosphorylase activity, and a thymidylate kinase activity.

6. The oncolytic virus of claim 5, wherein said suicide gene product is selected from the group consisting of codA::upp, FCY1::FUR1 and FCY1::FUR1[Delta] 105 (FCU1) and FCU1-8 polypeptides.

7. The oncolytic virus of claim 4, wherein said immunostimulatory protein is an interleukin or a colony-stimulating factor.

8. The oncolytic virus of claim 7, wherein said colony-stimulating factor is human GM-CSF.

9. The oncolytic virus of claim 1, wherein said one or more immune checkpoint modulator(s) comprises an antibody that specifically binds to human PD-L1.

10. The oncolytic virus of claim 9, wherein said antibody that specifically binds to human PD-L1 is selected from the group consisting of MPDL3280A and BMS-936559.

11. The oncolytic virus of claim 1, wherein said one or more immune checkpoint modulator(s) comprises an antibody that specifically binds to human CTLA-4.

12. The oncolytic virus of claim 11, wherein said antibody that specifically binds to human CTLA-4 is selected from the group consisting of ipilimumab, tremelimumab and single chain anti-CTLA4 antibodies.

13. A pharmaceutical composition comprising an effective amount of the oncolytic virus of claim 1 and a pharmaceutical acceptable vehicle.

14. The pharmaceutical composition of claim 13 comprising from approximately $10^7$ pfu to approximately $5 \times 10^9$ pfu of said oncolytic virus.

15. The pharmaceutical composition of claim 13, which is formulated for parenteral administration.

16. A method for treating a proliferative disease, comprising administering an oncolytic virus comprising inserted in its genome a nucleic acid molecule encoding one or more immune checkpoint modulator(s), wherein said virus is a vaccinia virus defective for thymidine kinase (TK) resulting from inactivating mutations in the J2R viral gene and defective for Ribonucleotide reductase (RR) activity resulting from inactivating mutations in only the viral I4L gene, and wherein said one or more immune checkpoint modulator(s) is selected from antibodies that specifically bind to PD-L1, PD-L2, LAG3, Tim3, BTLA, or CTLA4.

17. The method according to claim 16, wherein said proliferative disease is a cancer.

18. The method according to claim 17, wherein said cancer is selected from the group consisting of melanoma, renal cancer, prostate cancer, breast cancer, colorectal cancer, lung cancer, and liver cancer.

19. The method according to claim 16, wherein said oncolytic virus is administered by intravenous or intratumoral route.

20. The method according to claim 16, which comprises from 2 to 5 intravenous or intratumoral administrations of $10^8$ or $10^9$ pfu of oncolytic vaccinia virus at approximately 1 or 2 weeks interval.

21. The method according to claim 16, which further comprises administration of a prodrug and/or a substance effective in anticancer therapy.

\* \* \* \* \*

SEQUENCE LISTING

```
<160> NUMBER OF SEQ ID NOS: 2

<210> SEQ ID NO 1
<211> LENGTH: 478
<212> TYPE: PRT
<213> ORGANISM: artificial sequence
<220> FEATURE:
<223> OTHER INFORMATION: amino acid sequence for anti PD-1 heavy chain

<400> SEQUENCE: 1

Met Gly Leu Gly Leu Gln Trp Val Phe Phe Val Ala Leu Leu Lys Gly
1               5                   10                  15

Val His Cys Glu Val Arg Leu Leu Glu Ser Gly Gly Gly Leu Val Lys
            20                  25                  30

Pro Glu Gly Ser Leu Lys Leu Ser Cys Val Ala Ser Gly Phe Thr Phe
        35                  40                  45

Ser Asp Tyr Phe Met Ser Trp Val Arg Gln Ala Pro Gly Lys Gly Leu
    50                  55                  60

Glu Trp Val Ala His Ile Tyr Thr Lys Ser Tyr Asn Tyr Ala Thr Tyr
65                  70                  75                  80

Tyr Ser Gly Ser Val Lys Gly Arg Phe Thr Ile Ser Arg Asp Asp Ser
                85                  90                  95

Arg Ser Met Val Tyr Leu Gln Met Asn Asn Leu Arg Thr Glu Asp Thr
            100                 105                 110

Ala Thr Tyr Tyr Cys Thr Arg Asp Gly Ser Gly Tyr Pro Ser Leu Asp
        115                 120                 125

Phe Trp Gly Gln Gly Thr Gln Val Thr Val Ser Ser Ala Thr Thr Thr
    130                 135                 140

Ala Pro Ser Val Tyr Pro Leu Ala Pro Ala Cys Asp Ser Thr Thr Ser
145                 150                 155                 160

Thr Thr Asp Thr Val Thr Leu Gly Cys Leu Val Lys Gly Tyr Phe Pro
                165                 170                 175

Glu Pro Val Thr Val Ser Trp Asn Ser Gly Ala Leu Thr Ser Gly Val
            180                 185                 190

His Thr Phe Pro Ser Val Leu His Ser Gly Leu Tyr Ser Leu Ser Ser
        195                 200                 205

Ser Val Thr Val Pro Ser Ser Thr Trp Pro Lys Gln Pro Ile Thr Cys
```

Asn Val Ala His Pro Ala Ser Ser Thr Lys Val Asp Lys Lys Ile Glu
225                 230                 235                 240

Pro Arg Thr Asp Thr Asp Thr Cys Pro Asn Pro Pro Asp Pro Cys Pro
            245                 250                 255

Thr Cys Pro Thr Pro Asp Leu Leu Gly Gly Pro Ser Val Phe Ile Phe
        260                 265                 270

Pro Pro Lys Pro Lys Asp Val Leu Met Ile Ser Leu Thr Pro Lys Ile
            275                 280                 285

Thr Cys Val Val Val Asp Val Ser Glu Glu Pro Asp Val Gln Phe
        290                 295                 300

Asn Trp Tyr Val Asn Asn Val Glu Asp Lys Thr Ala Gln Thr Glu Thr
305                 310                 315                 320

Arg Gln Arg Gln Tyr Asn Ser Thr Tyr Arg Val Val Ser Val Leu Pro
                325                 330                 335

Ile Lys His Gln Asp Trp Met Ser Gly Lys Val Phe Lys Cys Lys Val
            340                 345                 350

Asn Asn Asn Ala Leu Pro Ser Pro Ile Glu Lys Thr Ile Ser Lys Pro
            355                 360                 365

Arg Gly Gln Val Arg Val Pro Gln Ile Tyr Thr Phe Pro Pro Pro Ile
    370                 375                 380

Glu Gln Thr Val Lys Lys Asp Val Ser Val Thr Cys Leu Val Thr Gly
385                 390                 395                 400

Phe Leu Pro Gln Asp Ile His Val Glu Trp Glu Ser Asn Gly Gln Pro
                405                 410                 415

Gln Pro Glu Gln Asn Tyr Lys Asn Thr Gln Pro Val Leu Asp Ser Asp
            420                 425                 430

Gly Ser Tyr Phe Leu Tyr Ser Lys Leu Asn Val Pro Lys Ser Arg Trp
        435                 440                 445

Asp Gln Gly Asp Ser Phe Thr Cys Ser Val Ile His Glu Ala Leu His
    450                 455                 460

Asn His His Met Thr Lys Thr Ile Ser Arg Ser Leu Gly Asn
465                 470                 475

<210> SEQ ID NO 2
<211> LENGTH: 233
<212> TYPE: PRT
<213> ORGANISM: artificial sequence
<220> FEATURE:
<223> OTHER INFORMATION: amino acid sequence for anti PD1 light chain

<400> SEQUENCE: 2

Met Ala Trp Thr Pro Gly Ile Phe Met Val Leu Ser Tyr Leu Thr Gly
1               5                   10                  15

Ser Phe Ser Tyr Glu Leu Thr Gln Pro Pro Ser Ala Ser Val Asn Val
            20                  25                  30

Gly Glu Thr Val Lys Ile Thr Cys Ser Gly Asp Gln Leu Pro Lys Tyr
        35                  40                  45

Phe Ala Asp Trp Phe His Gln Arg Ser Asp Gln Thr Ile Leu Gln Val
    50                  55                  60

Ile Tyr Asp Asp Asn Lys Arg Pro Ser Gly Ile Pro Glu Arg Ile Ser
65                  70                  75                  80

Gly Ser Ser Ser Gly Thr Thr Ala Thr Leu Thr Ile Arg Asp Val Arg
                85                  90                  95

Ala Glu Asp Glu Gly Asp Tyr Tyr Cys Phe Ser Gly Tyr Val Asp Ser

-continued

```
                    100                 105                 110
Asp Ser Lys Leu Tyr Val Phe Gly Ser Gly Thr Gln Leu Thr Val Leu
        115                 120                 125

Gly Gly Pro Lys Ser Ser Pro Lys Val Thr Val Phe Pro Pro Ser Pro
        130                 135                 140

Glu Glu Leu Arg Thr Asn Lys Ala Thr Leu Val Cys Leu Val Asn Asp
145                 150                 155                 160

Phe Tyr Pro Gly Ser Ala Thr Val Thr Trp Lys Ala Asn Gly Ala Thr
                165                 170                 175

Ile Asn Asp Gly Val Lys Thr Thr Lys Pro Ser Lys Gln Gly Gln Asn
                180                 185                 190

Tyr Met Thr Ser Ser Tyr Leu Ser Leu Thr Ala Asp Gln Trp Lys Ser
        195                 200                 205

His Asn Arg Val Ser Cys Gln Val Thr His Glu Gly Glu Thr Val Glu
        210                 215                 220

Lys Ser Leu Ser Pro Ala Glu Cys Leu
225                 230
```